(12) United States Patent
Babjack et al.

(10) Patent No.: US 11,165,909 B2
(45) Date of Patent: *Nov. 2, 2021

(54) SYSTEMS AND METHODS FOR PREDICTIVE PERSONALIZATION AND INTELLIGENT ROUTING

(71) Applicant: UnitedHealth Group Incorporated, Minnetonka, MN (US)

(72) Inventors: Destiny Babjack, Bethel Park, PA (US); Peter D. Howell, St. Paul, MN (US); Eric Bargman, St. Louis Park, MN (US); Tina Groat, Frisco, TX (US); Kevin Tan, Minnetonka, MN (US); Tom Kelly, Shorewood, MN (US); Sandra Long, St. Paul, MN (US); Sean McNattin, Dayton, MN (US); Mayank Kumar, Noida (IN); Lawrence Kevin Sundberg, Big Lake, MN (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/797,180

(22) Filed: Feb. 21, 2020

(65) Prior Publication Data

US 2020/0195781 A1 Jun. 18, 2020

Related U.S. Application Data

(63) Continuation of application No. 16/123,714, filed on Sep. 6, 2018, now Pat. No. 10,594,866, which is a
(Continued)

(51) Int. Cl.
*H04M 3/00* (2006.01)
*H04M 3/523* (2006.01)
(Continued)

(52) U.S. Cl.
CPC .......... *H04M 3/5233* (2013.01); *G16H 10/60* (2018.01); *G16H 20/10* (2018.01);
(Continued)

(58) Field of Classification Search
CPC ...... H04M 3/5233; G16H 80/00; G16H 40/20
(Continued)

(56) References Cited

U.S. PATENT DOCUMENTS 5,479,487 A * 12/1995 Hammond .............. H04M 3/51
379/266.07
6,591,112 B1 * 7/2003 Siccardo ................ G08G 1/205
455/521

(Continued)

*Primary Examiner* — William J Deane, Jr.
(74) *Attorney, Agent, or Firm* — Seyfarth Shaw LLP; Brian Michaelis

(57) ABSTRACT

Systems and methods for intelligently routing a member of an organization to a single point-of-contact within an optimized, secure network to address all the member's healthcare needs are described. The disclosed intelligent routing configurations transform and process, in real-time, vast amounts of member data to generate aggregated diagnoses and a member score specific to each member's household. The scores, among other things, are used to determine an identification of special needs and an appropriate advocate within the organization to route the member, and its account file containing real-time member and household level data.

18 Claims, 17 Drawing Sheets

Related U.S. Application Data continuation-in-part of application No. 15/820,503, filed on Nov. 22, 2017, now abandoned, which is a continuation of application No. 14/936,874, filed on Nov. 10, 2015, now Pat. No. 9,860,382.

(60) Provisional application No. 62/077,488, filed on Nov. 10, 2014.

(51) Int. Cl.

| | | |
|---|---|---|
| *G16H 80/00* | (2018.01) | |
| *G16H 20/10* | (2018.01) | |
| *G16H 50/30* | (2018.01) | |
| *G16H 50/70* | (2018.01) | |
| *G16H 10/60* | (2018.01) | |
| *G16H 40/20* | (2018.01) | |
| *G16H 50/00* | (2018.01) | |
| *H04M 3/51* | (2006.01) | |

(52) U.S. Cl.
CPC ............ *G16H 50/30* (2018.01); *G16H 50/70* (2018.01); *G16H 80/00* (2018.01); *G16H 40/20* (2018.01); *G16H 50/00* (2018.01); *H04M 3/5166* (2013.01); *H04M 2201/40* (2013.01); *H04M 2203/158* (2013.01); *H04M 2203/408* (2013.01); *H04M 2242/22* (2013.01)

(58) Field of Classification Search
USPC ....... 379/265.01–265.14, 266.01–266.1, 309
See application file for complete search history.

(56) References Cited

U.S. PATENT DOCUMENTS

| | | | | |
|---|---|---|---|---|
| 9,699,315 | B2* | 7/2017 | Waalkes | H04M 3/5235 |
| 10,580,305 | B2* | 3/2020 | Greenberger | G06Q 50/10 |
| 10,841,425 | B1* | 11/2020 | Langley | H04M 3/5183 |
| 10,868,913 | B1* | 12/2020 | Langley | H04M 3/5133 |
| 2002/0136381 | A1* | 9/2002 | Shaffer | H04M 3/4931 |
| | | | | 379/201.02 |
| 2005/0094798 | A1* | 5/2005 | Yacoub | H04M 3/5166 |
| | | | | 379/265.12 |
| 2005/0216551 | A1* | 9/2005 | Sirstins | H04M 3/5183 |
| | | | | 709/202 |
| 2006/0109975 | A1* | 5/2006 | Judkins | H04M 3/5233 |
| | | | | 379/265.02 |
| 2007/0038476 | A1* | 2/2007 | Sternlicht | G16H 40/20 |
| | | | | 705/2 |
| 2007/0198249 | A1* | 8/2007 | Adachi | G06F 40/205 |
| | | | | 704/9 |
| 2008/0043988 | A1* | 2/2008 | Galvin | H04M 3/51 |
| | | | | 379/265.11 |
| 2008/0095355 | A1* | 4/2008 | Mahalaha | H04M 3/5233 |
| | | | | 379/265.09 |
| 2009/0177405 | A1* | 7/2009 | Niggebrugge | G16H 50/70 |
| | | | | 702/19 |
| 2011/0010173 | A1* | 1/2011 | Scott | H04M 3/42221 |
| | | | | 704/235 |
| 2011/0130153 | A1* | 6/2011 | Davis | G06Q 90/00 |
| | | | | 455/456.1 |
| 2012/0219126 | A1* | 8/2012 | Odinak | H04M 3/53366 |
| | | | | 379/88.14 |
| 2012/0254196 | A1* | 10/2012 | Abramski | G16H 20/60 |
| | | | | 707/748 |
| 2012/0269338 | A1* | 10/2012 | Blanchard | H04M 3/5166 |
| | | | | 379/265.11 |
| 2014/0122109 | A1* | 5/2014 | Ghanbari | G16H 10/20 |
| | | | | 705/2 |
| 2014/0122118 | A1* | 5/2014 | Farr | G16H 40/67 |
| | | | | 705/3 |
| 2014/0143018 | A1* | 5/2014 | Nies | G06Q 30/016 |
| | | | | 705/7.32 |
| 2015/0106119 | A1* | 4/2015 | McCafferty | G16H 10/60 |
| | | | | 705/3 |
| 2015/0161241 | A1* | 6/2015 | Haggar | G06F 16/3329 |
| | | | | 707/723 |
| 2015/0195406 | A1* | 7/2015 | Dwyer | G06F 21/6254 |
| | | | | 379/265.07 |
| 2016/0078456 | A1* | 3/2016 | Chakraborty | G06Q 30/0204 |
| | | | | 705/7.31 |
| 2016/0239848 | A1* | 8/2016 | Chang | G06Q 30/016 |
| 2016/0277575 | A1* | 9/2016 | Alexander | H04M 3/5166 |
| 2016/0358277 | A1* | 12/2016 | Donhoff | G06Q 50/22 |
| 2017/0026514 | A1* | 1/2017 | Dwyer | H04M 3/5175 |
| 2017/0109479 | A1* | 4/2017 | Vemireddy | G06Q 50/22 |
| 2017/0193178 | A9* | 7/2017 | Di Lascia | G06F 19/328 |
| 2017/0208175 | A1* | 7/2017 | Jayapalan | H04M 3/42221 |
| 2018/0075518 | A1* | 3/2018 | Werbitt | G06Q 30/02 |
| 2019/0199759 | A1* | 6/2019 | Anderson | G06Q 50/205 |
| 2020/0045177 | A1* | 2/2020 | Langley | H04M 7/0027 |

* cited by examiner

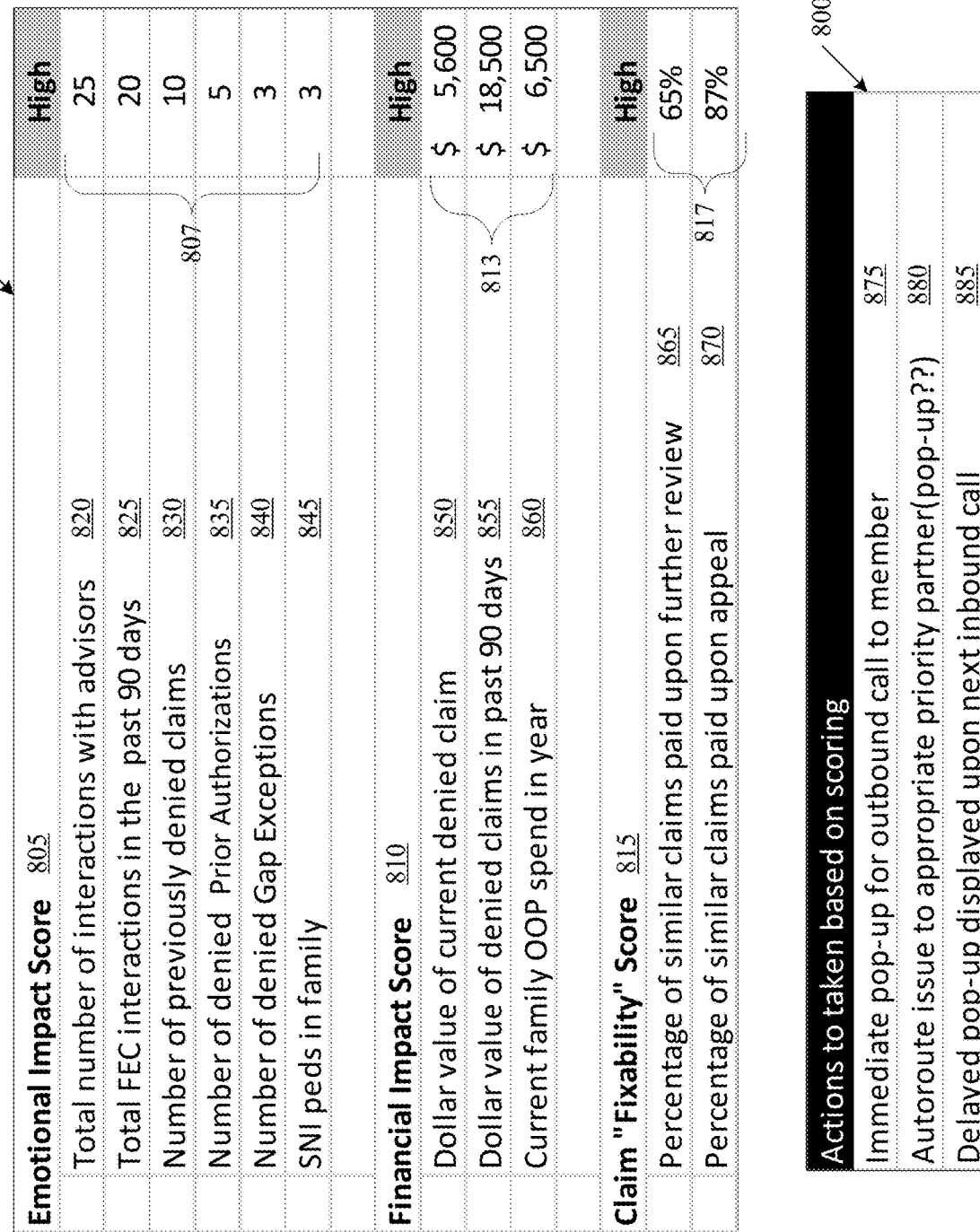

SYSTEMS AND METHODS FOR PREDICTIVE PERSONALIZATION AND INTELLIGENT ROUTING

CROSS-REFERENCE TO RELATED APPLICATION DATA

This application is a continuation of U.S. patent application Ser. No. 16/123,714 filed Sep. 6, 2018, which is a continuation-in-part of U.S. patent application Ser. No. 15/820,503, filed Nov. 22, 2017, which is a continuation of U.S. patent application Ser. No. 14/936,874, filed Nov. 10, 2015 which claims priority to U.S. Provisional Patent Application Ser. No. 62/077,488, filed Nov. 10, 2014, the contents of all of which are incorporated herein by reference in its entirety.

FIELD OF TECHNOLOGY

The present disclosure relates generally to secure networks, and more particularly to intelligent routing of data within a network.

BACKGROUND

One in five families in the United States has a child with special needs. In a given year, a family with a special needs member submits thirteen times as many claims as families without special needs members. Those families also spend approximately eighty-one times more out of pocket and see five times as many physicians, consuming critical and expensive resources. Often the source of the special needs arise from a rare and/or ambiguous disease that medical professionals, healthcare advocates and others have difficulty classifying or treating. The technical difficulty of diagnosing or classifying a member's condition or need leads to a member being on a diagnostic odyssey in search of an accurate diagnosis and access to specialized services available for that diagnosis. Traveling on a diagnostic odyssey due to a rare disease or the inability to properly diagnose a disease can lead to service denials, require appeals, higher out-of-pocket expenses, numerous visits to medical providers, and other onerous and detrimental consequences. Technical and financial resources are diverted or unnecessarily consumed/wasted.

Trying to navigate the complex landscape of service or care delivery, and social service providers, while balancing the care of family members with special needs, can leave families feeling frustrated, confused, financially stressed, tired, and in some situations hopeless. While families that have members with special needs use and rely on the healthcare system significantly more than any other population, often times those families are not equipped to traverse the complexities and intricacies of the system in a manner that maximizes the intended benefits offered to such families.

Further complicating access to appropriate healthcare services is the lack of intelligent routing of member calls and requests for information. Individuals contact organizations on a daily basis for a variety of reasons. In the past, organization representatives received and routed calls based on verbal caller input. Nowadays, however, organizations routinely have networks with automated systems that receive and route calls within the network. The automated systems sometimes use natural language or intelligent routing technologies that route incoming calls using data and/or voice input of a caller.

Current technologies may use caller ID and natural language technologies to route a call to a specific representative group of an organization. However, current technologies are not tailored to the complexities of special needs, and do not provide organization representatives with intelligent routing coupled with broad access to caller data in real-time. Known systems are generally not designed and configured in a manner to adequately capture and translate the service needs of a special needs caller while routing calls and data.

For example, callers typically have concerns or issues that require analysis by many points of contact across an organization. These points of contact are often disparate and disconnected, requiring a caller to call many areas of an organization or the caller being re-directed several times before having their problems adequately addressed by appropriate resources within the organization.

SUMMARY

The present disclosure generally provides an intelligent and data-driven system, tailored to special needs requirements, for predicting, identifying, tracking and routing requests for information from members of an organization. Systems and methods according to the disclosure solve the technical problems associated with limited intelligence and data association and provide access to information and intelligent routing for members of an organization with special needs or considerations. The system and method of the present disclosure is configured to predict, detect, alert and intelligently route to provide information to members of an organization who have special needs.

In one aspect, the disclosure provides for intelligent analysis and routing of calls, such as those processed through Interactive Voice Response (IVR) systems, within an organization. Improved systems and methods according to the disclosure use an automatic number identification processor (ANI), an improved conversation management processor (CM), and natural language processor to provide an organization member with a single organization point-of-contact within an optimized network to address all the member's needs. The member and their household are identified using ANI or other authentication techniques, the caller's expressed, explicit need is identified using natural language processing techniques, and the member's implicit, anticipated needs are derived by the CM using associated data sources and a variety of independent analytic variables.

The CM includes a specially configured and tailored rules engine that filters data inputs from several data sources. The CM specifically applies rules to the data and determines the implicit or anticipated level, e.g., basic, complex, or clinical in nature, of call messaging presentation and representative/advocate support most appropriate for the member.

A member may contact the organization on behalf of themselves or another member of their household. Thus, the present disclosure provides for identification of the needs of multiple identifiable individuals of the member's household, thereby preventing the need to transfer the member to various organization advocates until all of the member's needs are addressed or resolved. Specifically, the systems and methodology disclosed herein enable the single organization point-of-contact within the optimized network to address all of a member's needs by providing the organization advocate with an exhaustive up-to-date record and tailored graphical user interface (GUI) encompassing data associated with all individuals of the member's household.

The improved conversation management processor of the present disclosure provides a member engagement solution that maintains a holistic, contextual record for each member, thereby allowing for quick and effective placement of a member with an appropriate organization advocate. This prevents various member complaints experienced under present technologies. The disclosed system and method avoids dropping of information, i.e. information collected during an interactive voice response not being transferred to the ultimate organization advocate. The disclosed system and method avoids long and confusing prompts and inadequate menu options for directing the member to the appropriate organization advocate. Similarly, the disclosed system and method avoids the ultimate advocate misunderstanding the context of the member's call.

The specific, sophisticated analytics performed by the intelligent conversation management processor on the member data translates complex member data into consumable data that organization advocates have at their fingertips when interacting with a member. In various embodiments, for example the system and method of the disclosure implemented in a healthcare association context, the analytics described herein enable the aggregation of several types of data, e.g., healthcare claims history data, demographics data, healthcare expenses data, behavioral data, geographic data, provider availability data, and the like.

One aspect of the improved conversation management system of the present disclosure provides advanced techniques for identification and notification of members of an organization in need of specialized services. According to a further aspect of the disclosure, a system may include intelligent routing capabilities configured to detect and predict when an individual or group of individuals, such as a family, may be on a diagnostic odyssey or be ambiguously diagnosed. Using the data-driven and rules-based classification of a member as ambiguously diagnosed, a further aspect of the present disclosure allows for the conversation management processor to more effectively establish communication between advocates (those working for and with the organization) and members with special needs. Aspects of the present system may provide for a communications system configured to proactively alert or otherwise establish communication between members requiring special needs and the organizational advocates assisting them.

A further aspect of the present disclosure provides a holistic GUI presented to the advocate. Information displayed in the GUI, including the reason for the member's call, allows the advocate to quickly address the member's needs and offer suggestions to the member, e.g., in a healthcare association context, opportunities for the member to improve their use of the healthcare industry and programs that may help the member improve their health and well-being.

The disclosed intelligent routing techniques streamline and simplify inbound communication from members of an organization such as healthcare plan members. The disclosed intelligent analysis and routing techniques use several data points to connect the member with an organization advocate most appropriately suited to address the member's concerns. The disclosed systems and methods provide improvements over present technologies by utilizing an improved conversation management processor, within a highly secure networked computing environment(s), that applies specific, tailored rules/logic to data from multiple sources.

BRIEF DESCRIPTION OF THE DRAWINGS

Embodiments of devices, systems, and methods are illustrated in the figures of the accompanying drawings, which are meant to be exemplary and non-limiting, in which like references are intended to refer to like or corresponding parts, and in which:

FIG. 8 depicts a scoring table 800*a* and an action table 800*b* for an exemplary alert. according to one aspect of the present disclosure;

DETAILED DESCRIPTION

Figure 1:
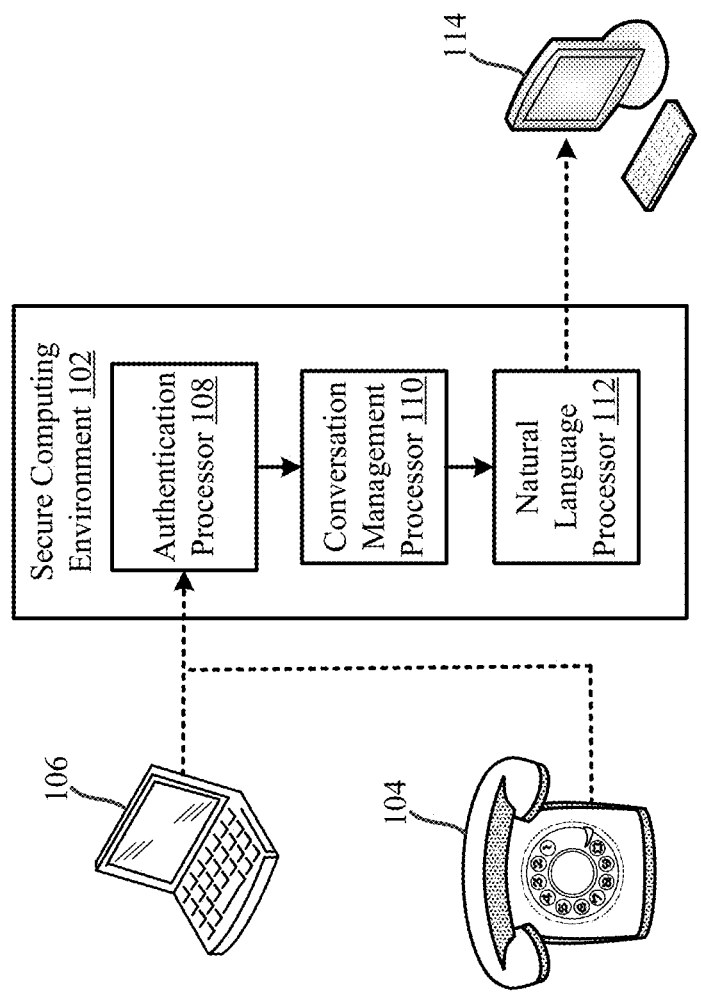
FIG. 1 is an overview system diagram illustrating a system for implementing intelligent routing according to the disclosure.

The detailed description of the present disclosure set forth herein makes reference to the accompanying drawings, which show various embodiments by way of illustration. While these various embodiments are described in sufficient detail to enable those skilled in the art to practice the disclosure, it should be understood that other embodiments may be realized and that logical and physical changes may be made without departing from the spirit and scope of the disclosure. Thus, the detailed description herein is presented for purposes of illustration only and not of limitation. For example, the steps recited in any of the method or process descriptions may be executed in an order other than as presented and are not limited to the order presented. Moreover, references to a singular embodiment may include plural embodiments, and references to more than one component may include a singular embodiment.

The present disclosure provides a network including components for intelligent routing and extensive and specialized processes for transforming vast amounts of data, in the illustrative embodiment healthcare data, into consumable data, i.e., member and household level data, used for intelligently routing members to appropriate organization advocates within a network of interconnected computing devices. Since healthcare data, which is highly sensitive and personal, is involved in multiple embodiments disclosed herein, one skilled in the art should appreciate that the data processing and intelligent routing of the present disclosure occur in a highly secure, networked computing environment. While the illustrative embodiments described herein may relate to healthcare information, it should be appreciated that secure systems as described may be implemented according to the disclosure for intelligent routing and transformation of other types of sensitive information such as personal information, legal information, national security information, or the like. The sophisticated, specialized, and specially configured networked computing environment and processes described herein, for example, facilitate the intelligent routing of a member with access to a network to a single organization advocate within the network capable of handling all, or nearly all, of the member's needs.

The present disclosure gives members of an organization a single point-of-contact within an optimized, secure network to address all their needs as provided for by the advocate accessible through a correspondingly specially configured computing device within the network. The predictive personalization and intelligent routing configuration(s) described herein streamlines and simplifies inbound communication from members of an organization aiming to communicate efficiently and effectively communicate with the organization through technology implemented communication channels. The predictive personalization and intelligent routing configuration(s) use several data points to connect the member with an advocate who can most appropriately address the member's concerns. Illustrative data points, for example in a healthcare implementation, used in determining routing include demographic data, recent medical or pharmacy claims data, clinical program enrollments and/or opportunities data, current health state data, incentive opportunities data, health risk assessment results data, and the like. The herein disclosed systems and methods provide improvements over present technical environments by using an intelligent conversation management processor and specially configured data sources to more precisely route calls, especially as relating to special needs considerations, to appropriate advocates within the network. The intelligent routing described herein is not limited to typical channels of service, e.g., telephone via IVR (Interactive Voice Response). Rather, the intelligent routing may be applied to various channels of communication such as instant messaging and email, for example.

Referring to FIG. 1, an overview diagram illustrating a system for intelligently routing a call or electronic communication from a member of an organization to an appropriate advocate connected for communication within the network is described. The system includes a secure computing environment or network 102. Various embodiments described herein involve sensitive and/or personal information. Thus, it should be appreciated that the secure computing environment 102 is not a general purpose computing environment. Rather, the secure computing environment 102 implements specially configured security parameters, and may be part of a highly secure network of multiple secure computing environments complying with appropriate security requirements.

A member contacts the secure computing environment 102 via a telephone 104 or a computing device 106. The member's communication is first directed to an authentication processor 108, which authenticates the member with a member file (in storage within the secure computing environment 102). For example, the authentication processor 108 may perform automatic number identification (ANI) processes to obtain caller ID data that can be referenced against caller ID data contained within member files within the secure computing environment 102. It should be appreciated, however, that authentication techniques other than ANI may be implemented in accordance with the present disclosure.

Once authenticated, the member's information/data is processed using specific rules of a conversation management processor 110. The conversation management processor 110, generally determines an implicit or anticipated level of call messaging presentation and advocate support most appropriate for the member. This is also referred to herein as intelligent routing of the member, and is described in greater detail hereinafter. For example, the conversation management processor 110 may label the member's need as basic, complex, or clinical in nature.

A natural language processor 112 analyzes the spoken words of the member to isolate the member's expressed or explicit need. Once processing by the conversation management processor 110 and natural language processor 112 is complete, the member call or communication link is routed to an appropriate advocate's terminal (e.g. call center terminal) of the organization and the member's file with appropriate data as determined based on rules, e.g. processed by the conversation management processor 110, is transmitted to the advocate's device 114.

Figure 2:
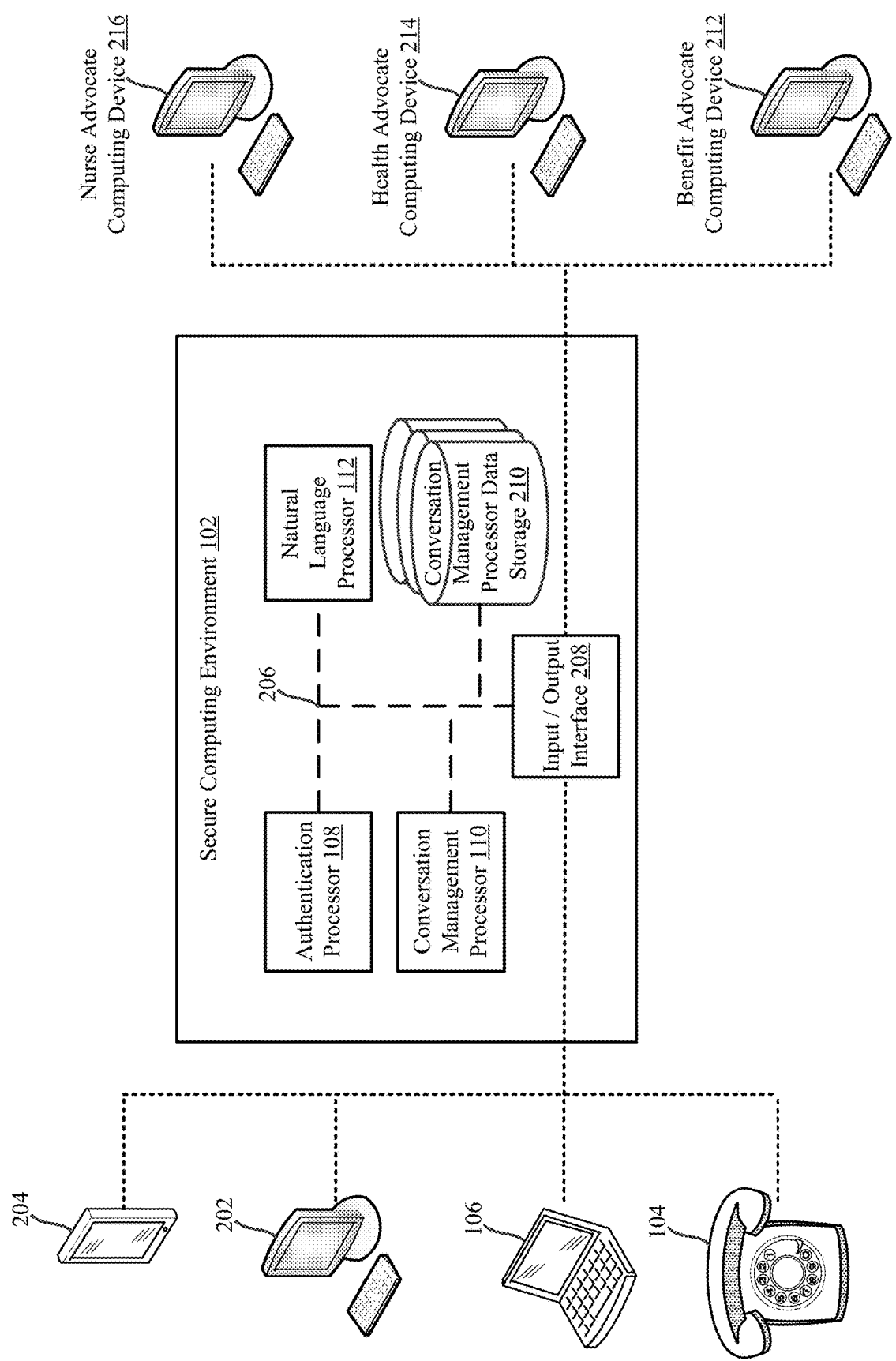
FIG. 2 is a detailed system diagram illustrating implementation of a special needs intelligent routing system for a member of an organization to an appropriate organization advocate within a specially configured communication network.

Referring now to FIG. 2, the system of FIG. 1 for intelligent routing of a member of an organization connecting to the network to an appropriate advocate within the secure network is described in greater detail. A member may interact with the secure computing environment 102 using various technologies, e.g., audibly via the telephone 104, or electronically using the laptop 106, a desktop computer 202, or via an application on a smart device 204. The smart device 204 may be a smart phone, tablet, or other like device that implements software in the form of software applications.

The components of the secure computing environment 102 may be connected via one or more buss(es) 206. In addition, various components of the secure computing environment 102 may be connected through direct linkages. The secure computing environment 102 includes an input/output interface 208 that enables the secure computing environment 102 to communicate data, control signals, data requests, and other information with other devices including computers, data sources, storage devices, and the like. The input/output interface 208 may be configured to communicate via wired or wireless connections. One skilled in the art should appreciate that the secure computing environment 102 may receive audio, image, text, video, and other inputs and transmit tailored user interface (UI) data to another computer or other source via the input/output interface 208.

When the member communicates with the secure computing environment 102, the member's communication is directed from the input/output interface 208 to the authentication processor 108. The authentication processor 108 determines the identity of the member, for example as described herein above with respect to FIG. 1. When a new member of the organization contacts the secure computing environment 102, the authentication processor 108 may not recognize the member's communication source, e.g., telephone 104, computer 106, 202, or smart device 204. When this occurs, the member may be requested to provide additional information, for example their member ID and/or date of birth (DOB) for authentication purposes. When the member subsequently contacts the secure computing environment 102, the authentication processor 108 uses, for example, ANI to automatically identify the member. For example, if the member uses the telephone 104, the authentication processor 108 is configured to identify the member based on the telephone number.

The secure computing environment 102 also includes the conversation management processor 110 and the natural language processor 112 as described herein. The natural language processor 112, while being configured to analyze the spoken words of a member, may also be configured to analyze the typed text of a member. If the member uses audible means of the telephone 104, computer devices 106, 202, or smart device 204, the natural language processor 112 directs simple, open-ended questions to the member and analyzes the member's responses to determine the member's explicit need(s). Use of the natural language processor 112 is beneficial because it eliminates the necessity of complicated phone trees.

The secure computing environment 102 further includes conversation management data storage 210. The conversation management data storage 210 houses data processed and/or generated by the conversation management processor 110 as described herein. In an illustrative embodiment, the present disclosure may be implemented within the healthcare industry. In this embodiment, the secure computing environment 102 may include several specially configured data stores such as, for example, a pharmacy claims storage, a program consumption storage, a medical claims storage, a screening results storage, an attitudinal data storage, a provider availability storage, a geographic data storage, a demographic data storage, and a cost of care storage. The aforementioned data stores may be implemented as standalone data stores within the secure computing environment 102, or they may be subcomponents of the conversation management data storage 210. One skilled in the art should appreciate that additional stores of data may be implemented as a function of the organization, network and services/products provided.

Upon the specific processes performed by the conversation management processor 110 being performed, and upon the member's explicit need(s) being ascertained by the natural language processor 112, the member connection is routed to an organization advocate within the network and the member's file is transmitted to the advocate's device. The advocate should be a person competent to handle most if not all of the member's needs. The organization's advocates may be segregated into tiers based on complexity of issues. For example, in a healthcare industry embodiment, the organization may have a Tier 1 benefit associate (illustrated as 212), a Tier 2 health advocate (illustrated as 214), and a Tier 3 nurse advocate (illustrated as 216). For example, the benefit advocate 212 may be a competent advocate when the member has infrequent health issues, i.e., the member is in good health and mainly needs routine/preventative care. The health advocate 214 may be a competent advocate when the member has complex claim issues, i.e., the member frequently contacts the secure computing environment 102 or is an out-of-network individual. The nurse advocate 216 may be a competent advocate when the member has significant health issues, i.e., the member has chronic, complex health issues or is identified as having special needs as described herein.

Figure 3:
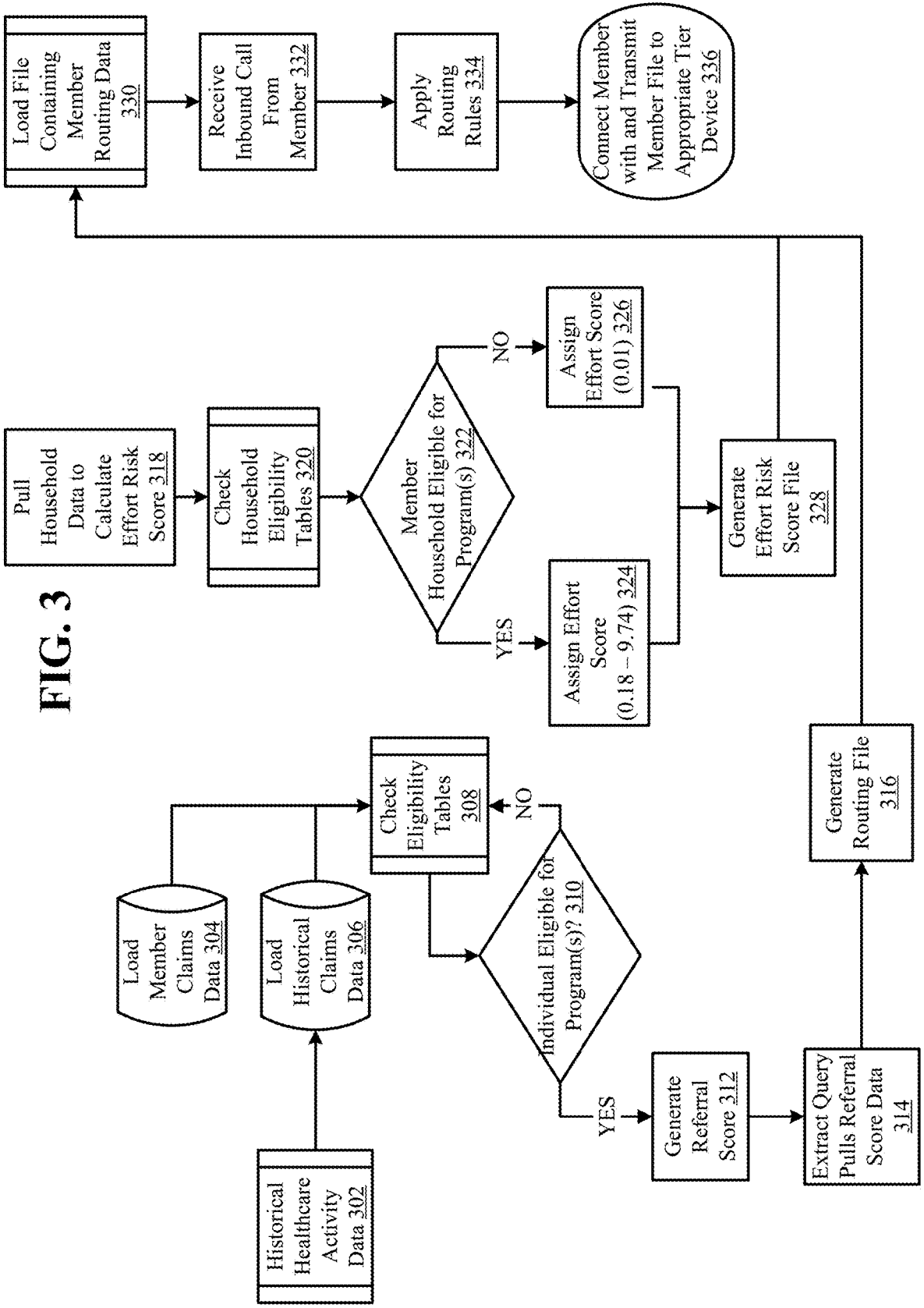
FIG. 3 is a process flow diagram illustrating a method for intelligent routing of a member of an organization to an appropriate organization advocate within a specially configured communication network of FIG. 2.

Attention is now given to FIG. 3, which illustrates an overview of processing for intelligent routing a member connection and its account file to an appropriately tiered advocate and its computing device. In a health care embodiment context, when an individual becomes a member of the organization, historical healthcare activity data of the member is obtained (illustrated as 302) to be maintained or accessible to the secure network 102. The historical healthcare activity data may include medical claims data, pharmacy claims data, biometrics results data, and demographic data, for example. In an example, the member may provide the historical activity to the secure computing environment 102 via a user interface of a computing device 106, 202, 204. Alternatively, for example, the member may provide the secure computing environment 102 authorization to obtain historical healthcare activity data from various sources, e.g., hospital computing environments, doctors office computing environments, and the like. The secure computing environment 102 may actively retrieve or passively obtain the historical healthcare activity data from the various sources on a periodic basis, e.g., weekly, daily, etc. The received historical healthcare activity data is stored within the various data stores of the secure computing environment 102, as illustrated in FIG. 2.

Various healthcare data of the member is loaded by the secure computing environment 102. Both post-membership enrollment claims data and pre-membership historical claims data may be loaded (illustrated as 304 and 306 respectively). Post-enrollment claims data of a member may be stored, i.e., refreshed, into the secure computing environment 102 on a periodic basis, e.g., weekly, daily, hourly, etc. Thereafter, program eligibility tables are checked against the loaded claims data (illustrated as 308). The tables may be in structured query language (SQL) format. The eligibility tables contain eligibility requirements for various programs offered by the organization that operates and maintains the secure computing environment 102. The secure computing environment 102 may check the member's claims data against the eligibility tables on a periodic basis, e.g., monthly, weekly, daily, etc.

By checking the member's claims data (both historical and post-enrollment) against the program requirements within the eligibility tables, the member's program eligibility(ies) is determined (illustrated as 310). If the member's claims data does not satisfy a single program's eligibility requirements, the eligibility tables are re-checked (illustrated as 308). Re-checking of the eligibility tables may occur on a periodic basis, such as monthly, weekly, daily, etc. Alternatively, if the member's claims data satisfies at least one program's eligibility requirements, a referral score(s) for the member is generated (illustrated as 312). If the claims data satisfies more than one program's requirements, a referral score may be generated for each eligible program. However, one skilled in the art should also appreciate that a single referral score may be generated for multiple eligible programs.

In a healthcare context, a referral score may be equated to the propensity of the member to contact the organization regarding the eligible program. Each referral score is derived from multiple variables, such as pharmacy first fill data, treatment decision support (TDS) program referral data, a pharmacy value factor score, an impact pro cost risk score, a monetized value, a household opportunity value, comprehensive medication review (CMR) program data, and a cost risk score, for example. The cost risk score may be based on claims data, and optionally, it may also be based on a service index score.

The decision whether to route a member and its account file to a Tier 3 nurse advocate level and its device 230 may be based on the member's referral score across multiple domains. For example, if the member's referral score surpasses a single requisite threshold, the member connection and its account file may be routed to the Tier 3 nurse advocate level and its device 230. The referral score(s) of a member may determine spend risks associated with the member. This may be based on the member's healthcare utilization data. Referral score data of the member is pulled using extract queries (illustrated as 314) and a routing file for the member is generated (illustrated as 316).

Still referring to FIG. 3, the member's household healthcare activity data is pulled to calculate an effort risk score (illustrated as 318). The member's household data may include medical claims data, pharmacy claims data, biometrics results data, and demographic data, for example, for each individual in the member's household. Household program eligibility tables are thereafter checked (illustrated as 320). The household tables may be in structured query language (SQL) format. The household eligibility tables may contain eligibility requirements for various household level programs offered by the organization that operates and maintains the secure computing environment 102. Thus, the member household data checked against the household eligibility tables includes data corresponding to various individuals within the member's household. For example, the household eligibility tables may be checked on a periodic basis, e.g., monthly, weekly, daily, etc.

It is then determined whether the member's household, i.e., household healthcare activity data, satisfies any of the program eligibility requirements (illustrated as 322). Regardless of the determination, the member's record/account file is assigned an effort risk score. An effort risk score is based on a variety of independent variables, such as diagnosis data, demographics data, and outstanding claims data, for example. In a general sense, an effort risk score demonstrates the propensity of the member to call the organization. An effort risk score may be based on most frequently occurring diagnosis categories for the member's household. If the household healthcare activity data satisfies at least one program's eligibility requirements, the member's record is assigned an effort risk score of 0.18 to 9.74 (illustrated as 324). If, instead, the member's household healthcare activity data does not satisfy the eligibility requirements of a single program, the member's record is assigned an effort risk score of about 0.01 (illustrated as 326). Assignment of an 0.01 effort risk score may result in the member and its account file being routed to a Tier 1 benefit advocate and its device 226 when the member contacts the organization. An effort risk file is thereafter generated for the member's account file (illustrated as 328).

The member's routing and effort risk files are loaded by the secure computing environment 102 (illustrated as 330). When this occurs, the member's routing data is analyzed to differentiate whether the member is a new or existing member. If the member is an existing member, the member's account file is refreshed with the newly generated referral and effort risk score values. If, on the other hand, the member is a new member, an account file with the newly generated referral and effort risk score values is created for the member. When the member contacts the organization, the member is identified by the authentication processor 108 as described herein above (illustrated as 332). After authentication occurs, the conversation management processor 110 applies intelligent routing rules to the member's account file to determine which advocate Tier to transmit the member connection and its account file to (illustrated as 334). Various routing rules described herein below are used. Once the appropriate Tier is identified, the member is connected with and the member's account file is transferred to the appropriate tiered advocate and its device (illustrated as 336).

Figure 4A:
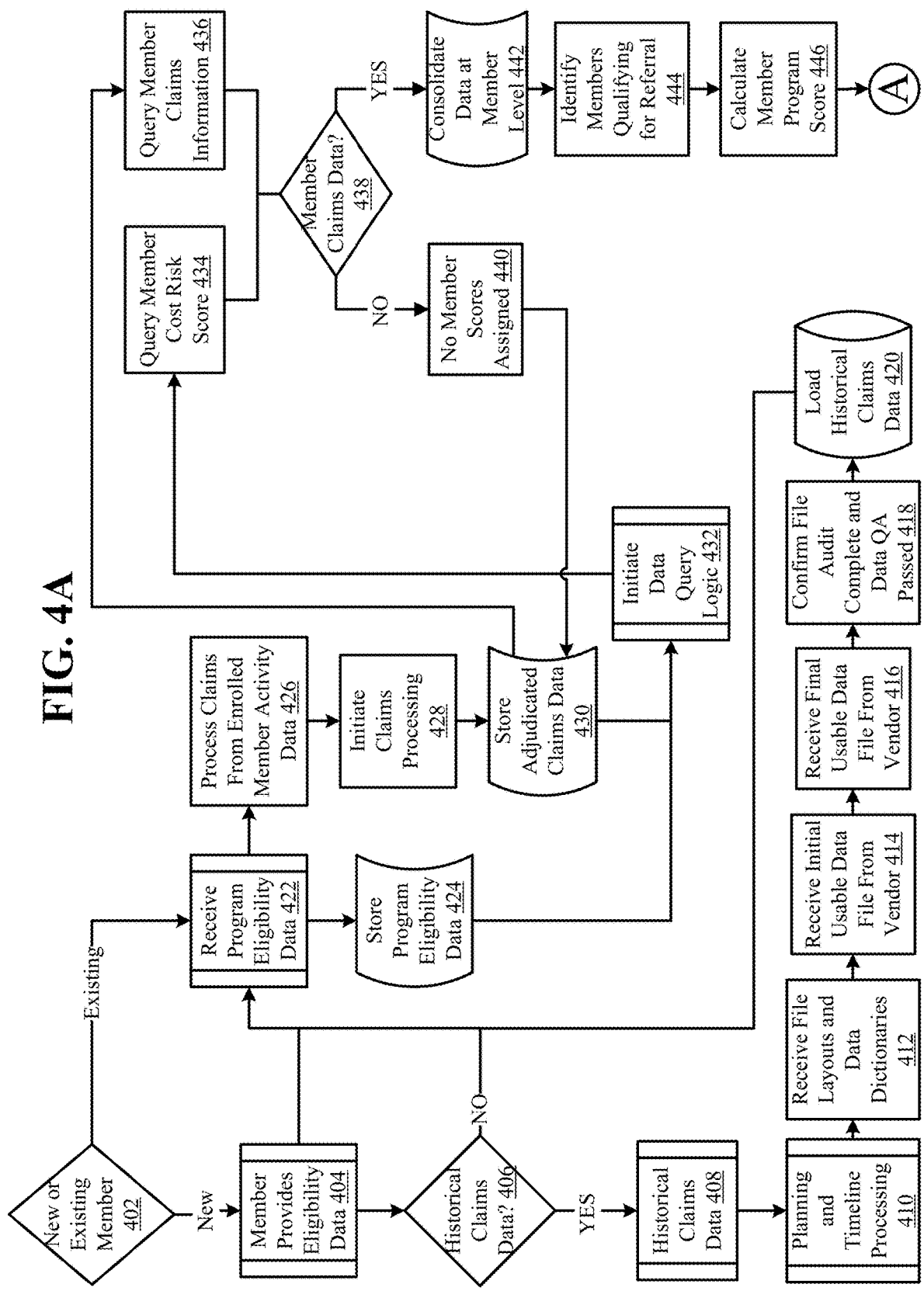
FIGS. 4A through 4C are process flow diagrams illustrating a method for intelligent routing of a member of an organization to an appropriate organization advocate within a communication network.
Figure 4B:
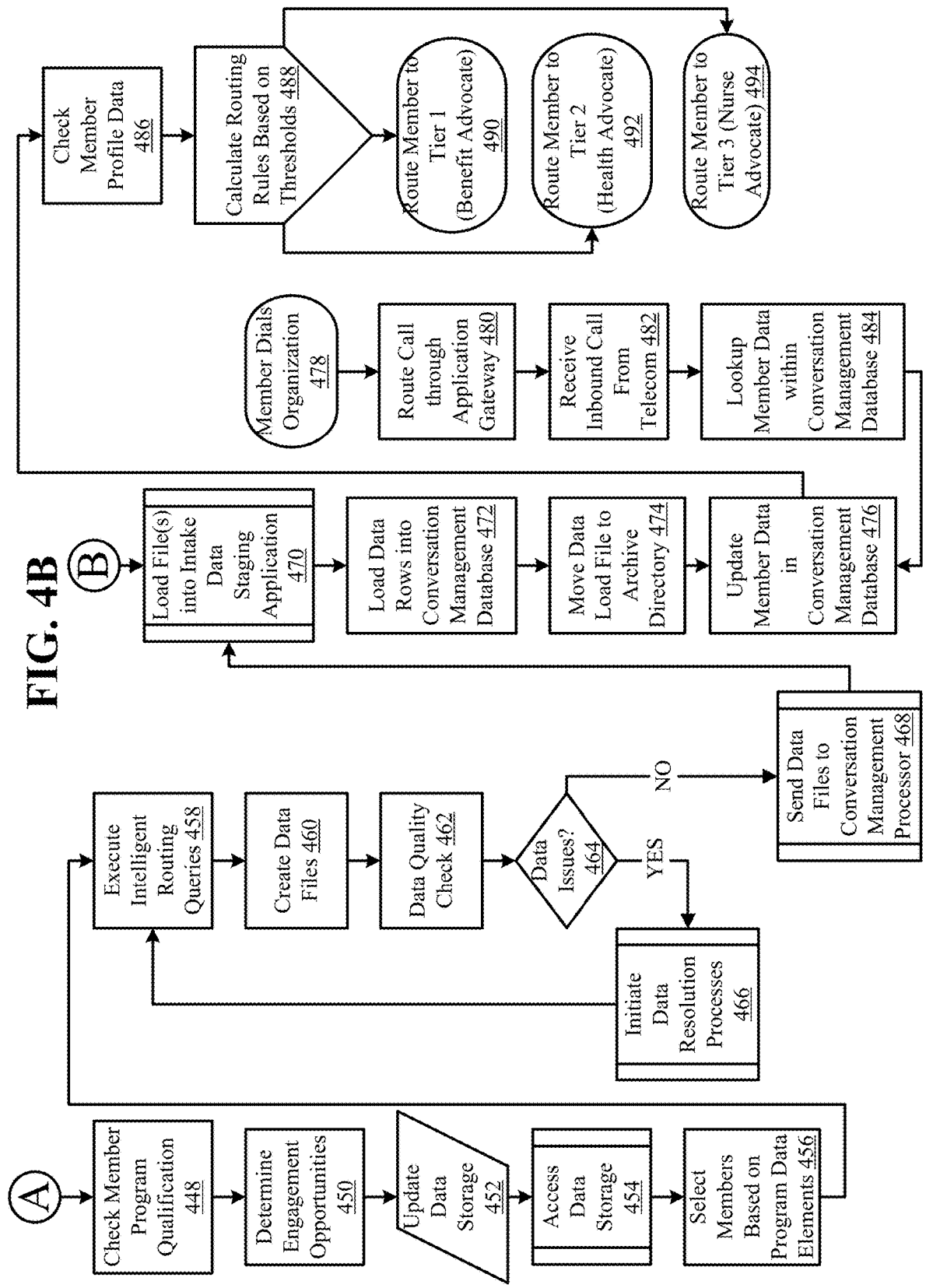
Figure 4C:
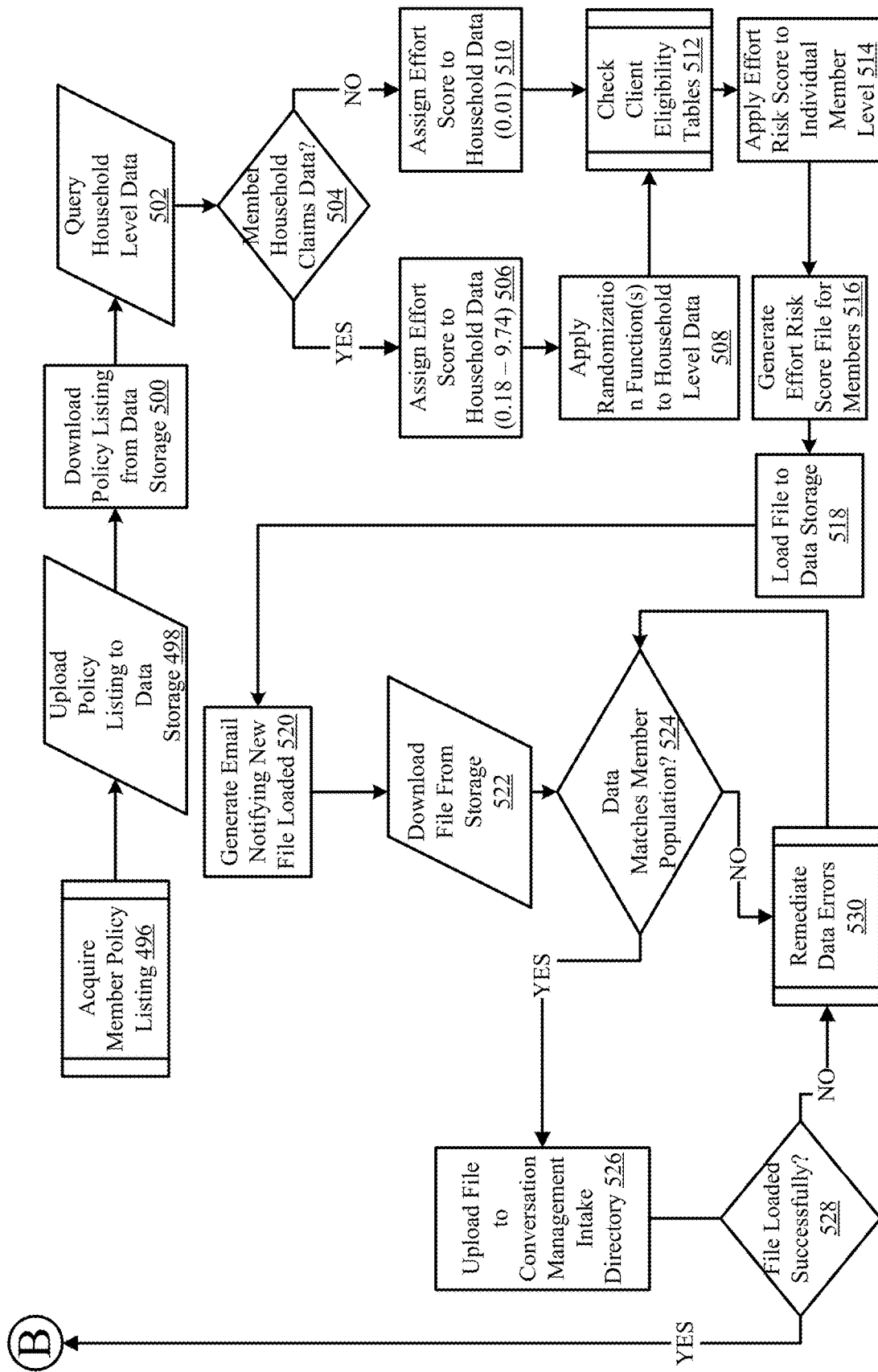

FIGS. 4A through 4C illustrate a method for intelligent routing of a connection of an organization's member and its account file to an appropriately tiered advocate and its computing device within the network. Referring specifically to FIG. 4A, it is determined whether the member is a new or existing member of the organization (illustrated as 402). This may entail the authentication processor 108 determining whether the member has an account file within the secure computing environment 102 and the comprehensiveness of any such account file. For example, a new member's account file may not contain historical healthcare claims data corresponding to claims made by the member prior to enrollment within the organization. Additionally, this may also entail the authentication processor 108 comparing demographic data provided by the member to demographic data stored within the secure computing environment 102.

If the member is new, the member may provide data demonstrating that they are eligible for one or more programs of the organization (illustrated as 404). This may involve the secure computing environment 102 providing the member, via a device, program eligibility requirements. Also, if the member is new, it is determined whether historical healthcare claims data will be provided to the secure computing environment 102 (illustrated as 406). Members may have the discretion of whether external, pre-membership claims data will be submitted upon enrollment with the organization.

If the member desires that external, pre-membership claims data be provided, such data is received by the secure computing environment 102 (illustrated as 408). In an example, the new member provides historical claims data to the secure computing environment 102 via a user interface of a computing device 106, 202, 204. Alternatively, for example, the new member may provide the secure computing environment 102 authorization to obtain healthcare claims data from various computing sources. Planning and timeline review processing of the historical claims data may be performed upon receipt of the data by the secure computing environment 102 (illustrated as 410).

The secure computing environment 102 may receive file layouts and data dictionaries for the historical claims data (illustrated as 412). Optionally, the secure computing environment 102 may receive an initial usable data file from the data source/vendor of the historical claims data (illustrated as 414). Thereafter, a final usable data file is received from the historical claims data source/vendor (illustrated as 416). It is then confirmed that the file audit process has been completed and that the data passed organization quality assurance standards (illustrated as 418). The organization may desire that step 418 be performed within a certain amount of days, e.g., 10, after receipt of the data. The member's historical claims data is then loaded into one or more storages of the secure computing environment 102 (illustrated as 420).

If the member is determined to be an existing member at step 402, if the member provides eligibility data at step 404, if historical claims data is not to be presented at step 406, or if the historical claims data is loaded at step 420, the secure computing environment 102 receives member program eligibility data (illustrated as 422). Upon receipt, the secure computing environment 102 stores the eligibility data (illustrated as 424) and/or processes claims from the enrolled member activity data (illustrated as 426). The enrolled member activity data may be received via a claims highway from healthcare providers. If the enrolled member activity data is to be processed at step 426, the secure computing environment 102 directs a relevant processor, e.g., the conversation management processor 110, to initiate claims processes (illustrated as 428). Claims processing is thereafter performed (not illustrated) and adjudicated claims data is stored (illustrated as 430).

Once the program eligibility data is stored at step 424, the secure computing environment 102 initiates data query logic (illustrated as 432). The logic/rules allow for data to be pulled from multiple sources, thereby enabling the secure computing environment 102 to act as a data repository for multiple systems to access. When steps 430 and 432 are complete, the member's cost risk score and claims information is queried (illustrated as 434 and 436 respectively). A cost risk score is applied to every member of the organization. At step 436, various information such as, for example, pharmacy data, medical claim data, and lab results data is queried for members of the organization.

It is then determined whether claims data exists for each of the organization's members (illustrated as 438). If no data exists for a member, no member score is assigned for the member (illustrated as 440) and the member's data is stored with the adjudicated claims data (illustrated as 430). Alternatively, if it is determined that claims data exists for various organization members, the claims data is consolidated on a member level (illustrated as 442) and members qualifying for a referral are identified (illustrated as 444). The referral determination of step 444 is performed on the member level, not the cumulative member household level. A member identified as qualifying for a referral is assigned a unique ID different from the member's member ID.

A program score for each member qualifying for a referral is thereafter calculated (illustrated as 446). Each program score relates to future spend risks based on member healthcare utilization data. Examples of healthcare utilization data include, for example, cost risk score, pharmacy first fill data, TDS program referral data, a pharmacy value factor score, a cost risk score, a monetized value, a household opportunity value, and CMR program data.

Referring to FIG. 4B, member program qualification is checked (illustrated as 448). This may involve the secure computing environment 102 reviewing member scores and program referral identifications to determine whether a member qualifies for a referral based on, for example, member opt out preferences, suppression logic, i.e., referral attempt thresholds, or member program enrollment, i.e., the member is already enrolled or has already participated in the program. Additionally, the secure computing environment 102 may determine member program qualification at step 448 based on program co-management rules, conflicting program rules, and hierarchy of program impact rules, for example.

The secure computing environment 102 also determines engagement opportunities (illustrated as 450). Engagement opportunities relate to qualified programs of members. For example, a low risk member may receive mail campaigns; a medium risk member may receive email and mail campaigns; and a high risk member may receive unsolicited, proactive organization outreach calls, as well as phone, email, and mail campaigns. Thereafter, a data storage containing program qualification/referral information and engagement opportunities information is updated (illustrated as 452).

The data storage containing the program qualification/referral information and engagement opportunities information is accessed (illustrated as 454) to extract data, and members are selected based on program data elements (illustrated as 456). For example, analyzed program data elements include pharmacy first fill data, value factor score, TDS program referral data, cost risk score, monetized value, household opportunity value, nurse monetized value, and CMR program data. Thereafter, the secure computing environment 102 instructs one or more processors therein to execute intelligent routing queries (illustrated as 458). An example processor includes the conversation management processor 110 described herein above. The intelligent routing queries are executed to extract data from the data storage of step 454. Extracted member specific data may be aggregated to household level data by the processor(s).

Once the household level data is generated, a file for the data of each household is created (illustrated as 460). The created files are full replace files, i.e., they replace any temporary household files generated at step 458. For example, the data of a household may be represented in two files: a routing logic file and a nurse monetized value file. A data quality check is performed on the household level files (illustrated as 462). Validation quality checks may be performed to compare counts, thereby ensuring populations of members have been successfully identified as qualifying for a referral(s).

After the quality check is performed, it is determined whether there are any data issues (illustrated as 464). If there are outstanding data issues, data resolution processes are initiated (illustrated as 466) and the secure computing environment 102 re-instructs a processor(s) to execute intelligent routing queries (illustrated as 458). Conversely, if no outstanding data issues remain, the household level data files are transmitted for processing by the conversation management processor 110 (illustrated as 468).

The conversation management processor 110 loads the household level files into an intake data staging application of the secure computing environment 102 (illustrated as 470). The data staging application receives files and prepares the files for loading into the conversation management processor data storage 210 of the secure computing environment 102. Preparation of the files may take seconds, minutes, hours, days, etc. depending upon implementation and the vastness of the files. Data rows are loaded into the conversation management processor data storage 210 (illustrated as 472). Each data row may be specific to a single household level file. Data load files are thereafter moved to an archive directory (illustrated as 474) and member data is updated in the conversation management processor data storage 210 (illustrated as 476). Once files have successfully updated member rows in the conversation management processor data storage 210, the conversation management processor 110 may properly interact with the household level files. For example, the conversation management processor 110 may properly route calls, perform dynamic prompting interactive voice response (IVR) member interaction, and provide screen popups and virtual call center desktops to advocate devices. Alternatively, the IVR member interaction may be performed by the natural language processor 112.

When a member calls/dials the organization (illustrated as 478), the call is routed through an application gateway request (illustrated as 480). At the application gateway, validation is performed to indicate whether the call should be directed through the conversation management processor 110 for appropriate call routing. This validation may be performed by the authentication processor 108. The call is thereafter received by the conversation management processor 110 (illustrated as 482) and data pertaining to the calling member is looked up in the conversation management processor data storage 210 (illustrated as 484). If any new member data is available, the member's data in the conversation management processor data storage 210 is updated (illustrated as 476).

After the conversation management data storage 210 is updated, the member's profile data is checked (illustrated as 486). The member's profile is validated/checked by the conversation management processor 110 using extension tables, which house member household routing data. All members of the organization can route to an advocate tier if member scores meet certain requirements described herein. The conversation management processor 110 then calculates routing rules based on thresholds (illustrated as 488). For example, based on values of tier routing values, the conversation management processor 110 may compare values to determine tier routing. The comparisons may include value thresholds as an "if/then" format.

Default routing causes the member to be routed to a Tier 1 advocate (illustrated as 490). Default routing occurs when the member's household does not have any data or the member's household data does not surpass any of the thresholds described with respect to steps 492 and 494 below. The member is routed to a Tier 2 advocate (1) if their effort risk score is greater than XX or (2) the member's monetized value is between YY and ZZ (illustrated as 492). The XX threshold is determined by using a ranking algorithm that assigns an effort risk value to a diagnosis. For example, if the household had the diagnosis that is listed on their claim in the past 30 days, it is assigned a value. The YY and ZZ thresholds are determined using subject matter expert knowledge and qualitative research to determine the dollar amount that is considered high value to the payor. The value may be derived based on typical costs of clinical treatments and assigned by the consumer or clinical nurse. Moreover, the member is routed to a Tier 3 advocate (1) if their monetized value is greater than X, (2) if the member's cost risk score is greater than or equal to Y, (3) if the member's pharmacy first fill equals "yes" (i.e., the member filled a new prescription for the first time in the past 30 days), or (4) if the member's pharmacy value factor is greater than or equal to Z and the member's CMR program data equals "yes" (i.e., yes is assigned when a member is filling multiple prescriptions and there is a likelihood that there are alternative prescriptions or potential drug interactions and the intervention of a pharmacist is required) (illustrated as 494). The X threshold is determined using subject matter expert knowledge and qualitative research to determine the dollar amount that is considered high value to both the member and organization. The value may be derived based on typical costs of clinical treatments and assigned by the consumer or clinical nurse. The level of Y is determined using subject matter expert knowledge and qualitative research to determine the dollar amount that is considered high cost to the payor. The value may be derived based on typical costs of clinical treatments and assigned by a quantitative algorithm within the health insurance organization. The Z threshold is determined based on the risk of having medication issues where pharmacist intervention is required and is calculated using an algorithm derived from historical data. As described, the thresholds of Tier 2 and Tier 3 routing are implemented as "OR" functions. However, one skilled in the art should appreciate that the Tier 2 and Tier 3 thresholds may be implemented as "AND" functions without departing from the present disclosure.

Referring specifically to FIG. 4C, the member's policy listing is acquired (illustrated as 496) and the policy listing is uploaded to a data storage of the secure computing environment 102 (illustrated as 498). The uploaded member policy may be added into effort risk score calculations. The policy listing is thereafter downloaded from the data storage (illustrated as 500) and member household level data is queried (illustrated as 502).

Based on the query, it is determined whether household level claims data for the member exists (illustrated as 504). If household level claims data exists, an effort score of 0.18 to 9.74 is assigned to the household data (illustrated as 506), and a randomization function(s) is applied to the member's household level data (illustrated as 508). The effort score may be based on a variety of independent variables, such as diagnosis data, demographics data, and outstanding claims data, for example. The randomization function(s) adjust member data scores evenly across member populations from 7.65 to 7.64 until a staffing call volume threshold, e.g., Tier 2 routing threshold has been satisfied. Conversely, if no member household level data exists, the member's file is assigned a household effort score of 0.01 (illustrated as 510).

After steps 508 and 510 occur, program eligibility tables are checked (illustrated as 512). The household level data may be expanded/transformed into individual member data related to a specific household in order to properly check the eligibility tables in a beneficial and expeditious manner. An effort risk score is then applied to the data on an individual member level (illustrated as 514). The highest frequency effort risk score of the member's household may be applied to the member's individual-level file. When this occurs, all of the individuals of a household receive the same effort risk score. This may result in all of the individuals of a household being intelligently routed the same way by the conversation manager processor 110. An effort risk score file is then generated for each member (illustrated as 516) and the member files are loaded into a data storage of the secure computing environment 102 (illustrated as 518).

An email may then be generated by the secure computing environment notifying an individual of the data file loading (illustrated as 520) and the data files are thereafter downloaded from the data storage (illustrated as 522). Download of the data file(s) may involve performing a query operation specific to policy number. The data file(s) may be summarized at the household level when downloaded. The data is then validated to determine whether the data matches the member population (illustrated as 524).

The data may be validated by comparing the data to count of membership by policy for, for example, missing policies, target population identified, membership policy volume count, and effort risk score distribution, i.e., risk bucket percentage. The validation processes may be performed prior to the data files being transmitted to the conversation management processor 110 and its corresponding data storage 210. Validation may involve verifying policy numbers within the data files and confirming the effort risk distribution of the data. A high effort risk score may be between 12% and 18%. When a data file is validated, the file is uploaded to a conversation management intake directory, e.g. in the conversation management processor data store, (illustrated as 526) and it is determined if the file was loaded successfully (illustrated as 528). File load success may be determined by checking the conversation management data store. A validating file may be in an archive folder of the conversation management data store. If the file load was unsuccessful or if the data was not validated, the data errors are remediated (illustrated as 530) and the data is re-validated (illustrated as 524). If the file was loaded successfully, the file is loaded into an intake data staging application (illustrated as 470).

Figure 5A:
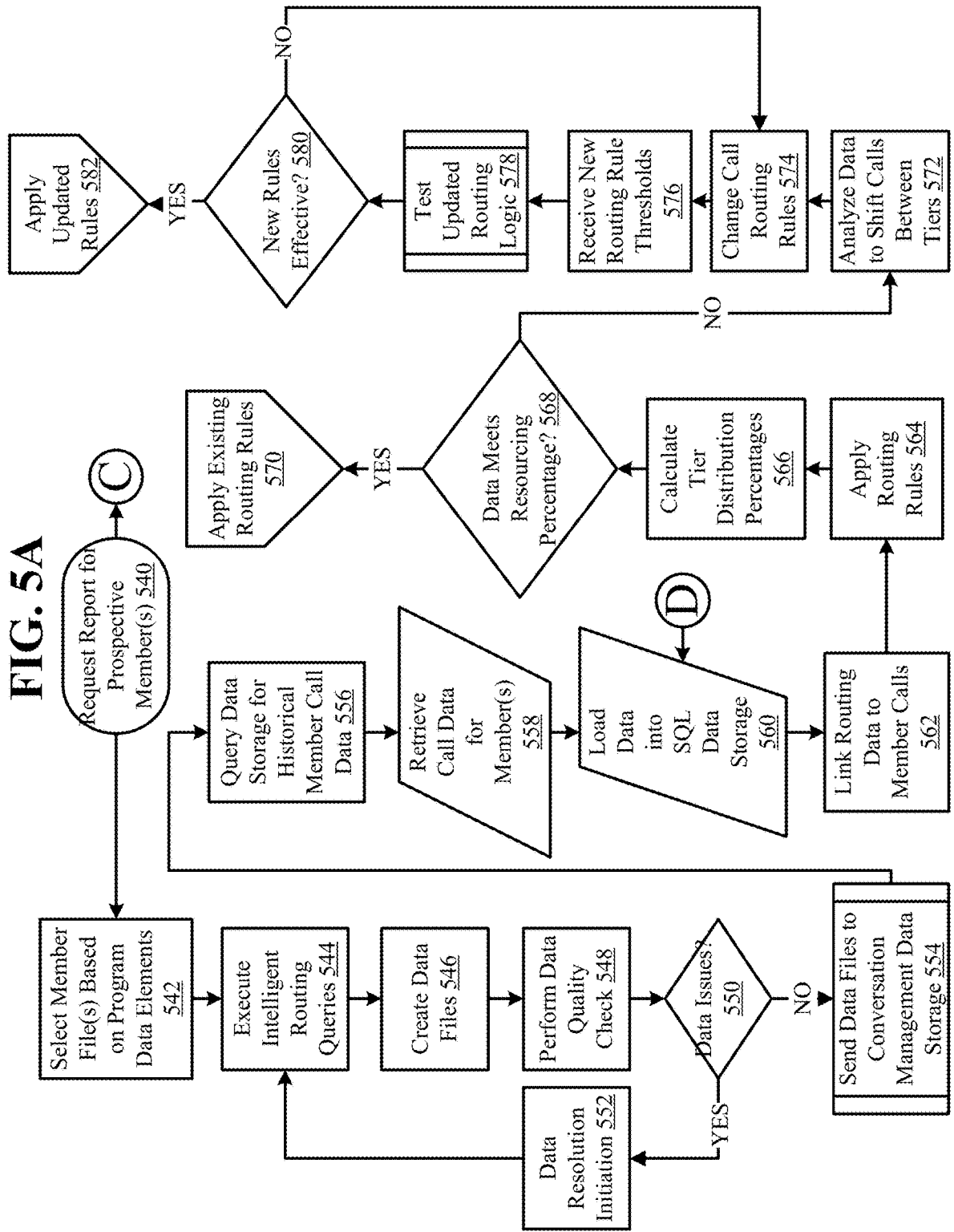
FIGS. 5A and 5B are process flow diagrams illustrating a method for performing a quality check on appropriateness of selected intelligent routing rules for intelligent routing of a member of an organization to an appropriate organization advocate within a communication network according to the disclosure.
Figure 5B:
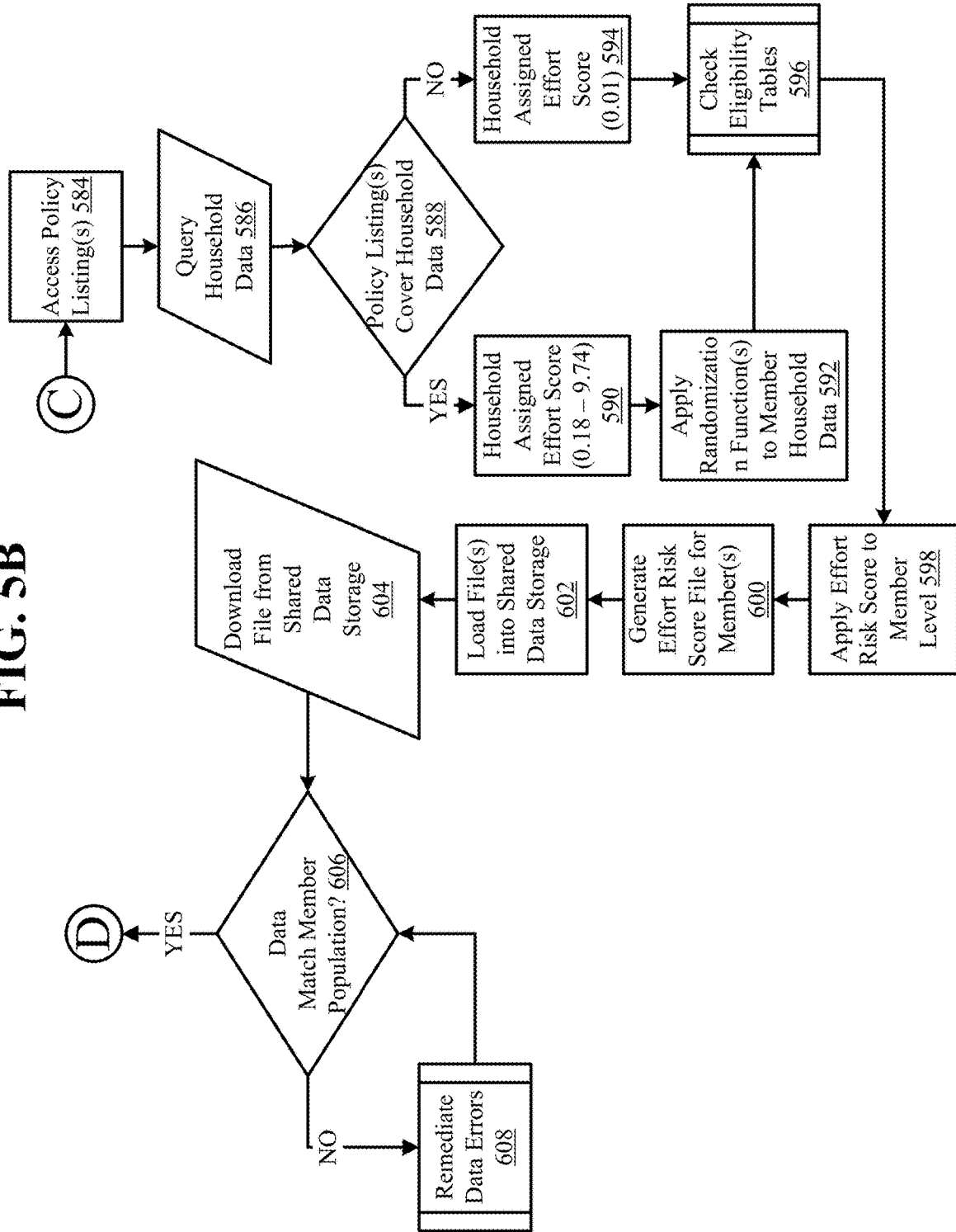

Attention is now given to FIGS. 5A and 5B, which illustrate a method for performing a quality check on the appropriateness of selected intelligent routing rules. As illustrated in FIG. 5A, the method begins with a request for a report for prospective member(s) (illustrated as 540). This may include a request for an ad hoc report, which is a mock up routing file for new onboarding members. In response, a mock routing file is selected based on program data elements (illustrated as 542). The secure computing environment 102 then instructs one or more processors therein to execute intelligent routing queries (illustrated as 544). Data files (either on the member level or household level) are created (illustrated as 546) and a data quality check is performed (illustrated as 548). During the quality check, it is determined whether issues exist within the data (illustrated as 550). If issues are identified, data resolution processes are initiated (illustrated as 552) and, thereafter, intelligent routing queries are re-performed on the data (illustrated as 544). If no issues exist in the data, the mock routing file is transmitted to the conversation management data storage 210 (illustrated as 554). In an example, the conversation management data storage 210 is in a structured query language (SQL) format.

A data storage of the secure computing environment 102 is then queried for historical member call data (illustrated as 556) and historical call data for one or more members is retrieved (illustrated as 558). The retrieved member call data and effort risk score data (sorted by member) are loaded into a specific data storage, such as an SQL data storage, for example (illustrated as 560). The routing data within the SQL data storage is linked to associated member call data also within the SQL data storage (illustrated as 562). For example, linkage of the data may occur at a household level. In another example, data variables that drive intelligent routing, e.g., thresholds and scores, are used to link the routing data to associated household level call data. Linking of the data builds a member specific mock up routing file for further analysis by the secure computing environment 102. The ad hoc report of step 540 is combined with current routing files to analyze rule adjustments for resource allocation routing.

Routing rules as described herein are applied to the linked data (illustrated as 564). Currently configured and implemented routing rules are applied to the member(s) specific mock routing file for analysis of household level call distribution across the tiers of organization advocates. Next, tier distribution percentages are calculated (illustrated as 566) and it is determined whether the present routing rules result in appropriate resourcing percentages/distributions (illustrated as 568). In other words, it is determined whether the routing percentages generated by the present routing rules meet a staffing resource structure of the organization's advocates. For example, appropriate percentages may be defined as 50% of inbound calls being routed to Tier 1 advocates, 30% of inbound calls being routed to Tier 2 advocates, and 20% of inbound calls being routed to Tier 3 advocates. If the percentages are appropriate, the existing, presently implemented routing rules are continually used to intelligently route member's and their account files (illustrated as 570). If, instead, the percentages produced by the presently implemented routing rules are inappropriate, the data is analyzed to shift member calls between advocate tiers in accordance with resourcing requirements (illustrated as 572).

Still referring to FIG. 5a, the implemented routing rules are thereafter changed (illustrated as 574) and new routing rule thresholds are received (illustrated as 576). For example, the routing rules may be changed to impact Tier 3 routing with respect to treatment decision support (TDS) and/or cost risk score. Additionally, the routing rules may be changed to impact Tier 2 routing with respect to effort risk score and/or monetized opportunity value. The new/updated routing rules are tested (illustrated as 578) and it is determined whether the new/updated routing rules are effective/appropriate, i.e., generate proper tier distribution percentages (illustrated as 580). Testing of the new routing rules may be performed using a testing application executed by the conversation manager processor 110. If the new routing rules/logic are inappropriate, the routing rules are changed again (illustrated as 574). To the contrary, if the routing rules/logic are effective/appropriate, the new routing rules are thereafter applied to intelligently route member's calls and the member's profile account (illustrated as 582).

As illustrated in FIG. 5B, in response to the report for prospective member(s) being requested at step 540, policy listing(s) are accessed (illustrated as 584) and a query is run on the household level data to extract it from storage (illustrated as 586). It is then determined whether the policy (ies) cover any of the household data (illustrated as 588). If a household is covered by the policy, an effort score of 0.18 to 9.74 is assigned to the household data (illustrated as 590), and a randomization function(s) is thereafter applied to the household data (illustrated as 592). The randomization function(s) adjust household scores evenly across household populations from 7.65 to 7.64 until a staffing call volume threshold, e.g., Tier 2 routing threshold has been satisfied. To the contrary, if a household is not covered by the policy, an effort score of 0.01 is assigned to the household data (illustrated as 594). After steps 592 and 594 are performed, program eligibility tables are checked (illustrated as 596).

Effort risk scores are then applied at the member level of the household data (illustrated as 598) and an effort risk score file for each member is generated (illustrated as 600, FIG. 5B). The member file(s) is loaded into a shared data storage, e.g. the conversation management processor data store. The stored member file(s) is thereafter downloaded from the shared data storage (illustrated as 604) and it is determined whether the downloaded data file(s) matches member population data (illustrated as 606). Step 606 may involve comparing data elements in the member file to data elements of population data, thereby often aligning and matching member identification number data stored in each file. If the data does not match the member population, the data errors are remediated (illustrated as 608) and the data is reprocessed for conformity with the member population (illustrated as 606). If, however, the data matches the member population, the data is loaded into the SQL data storage (illustrated as 560).

Figure 6A:
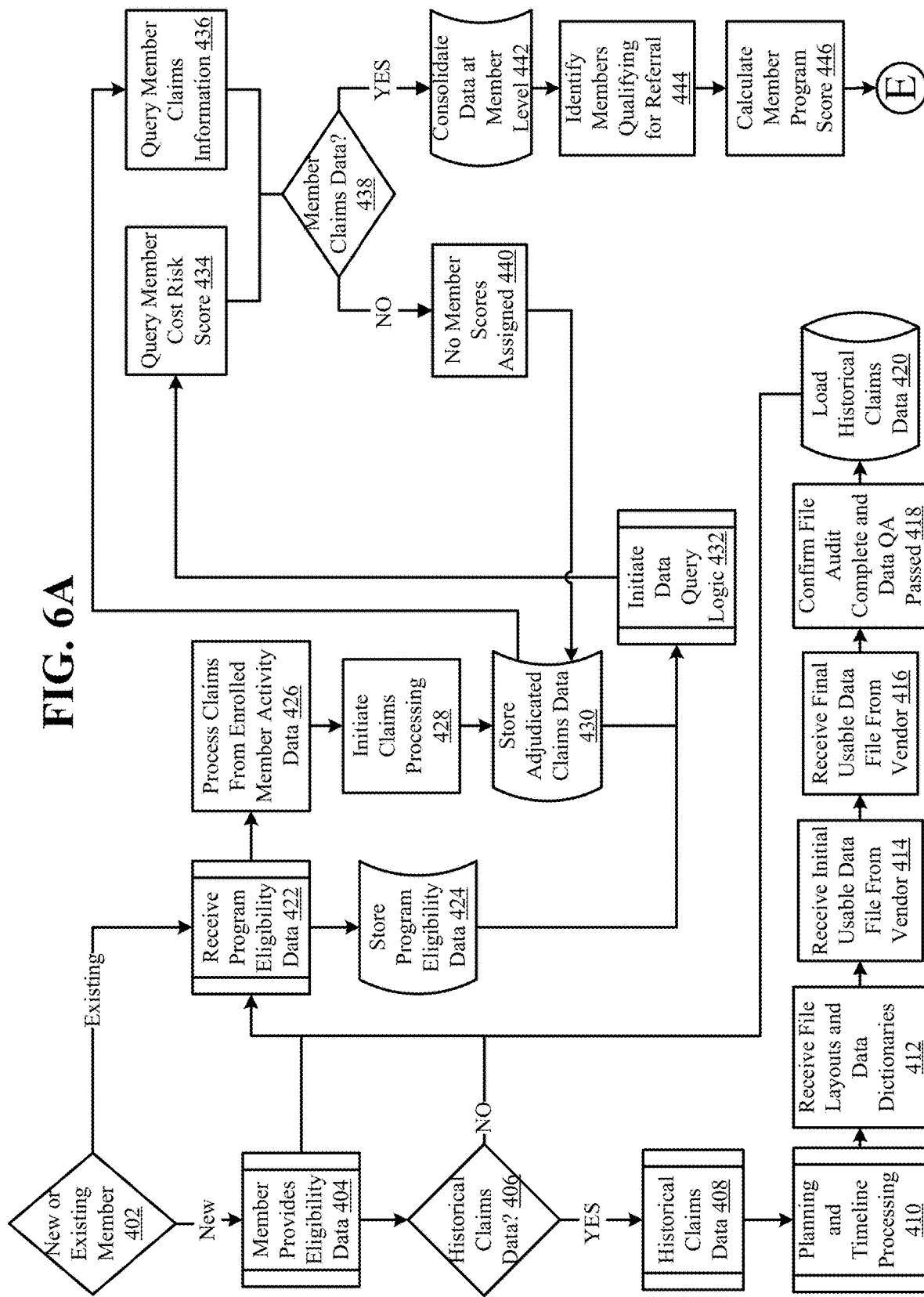
FIGS. 6A through 6C are process flow diagrams illustrating a further embodiment of the method of FIGS. 4A through 4C, for intelligent routing of a member of an organization to an appropriate organization advocate within a communication network according to the disclosure.
Figure 6B:
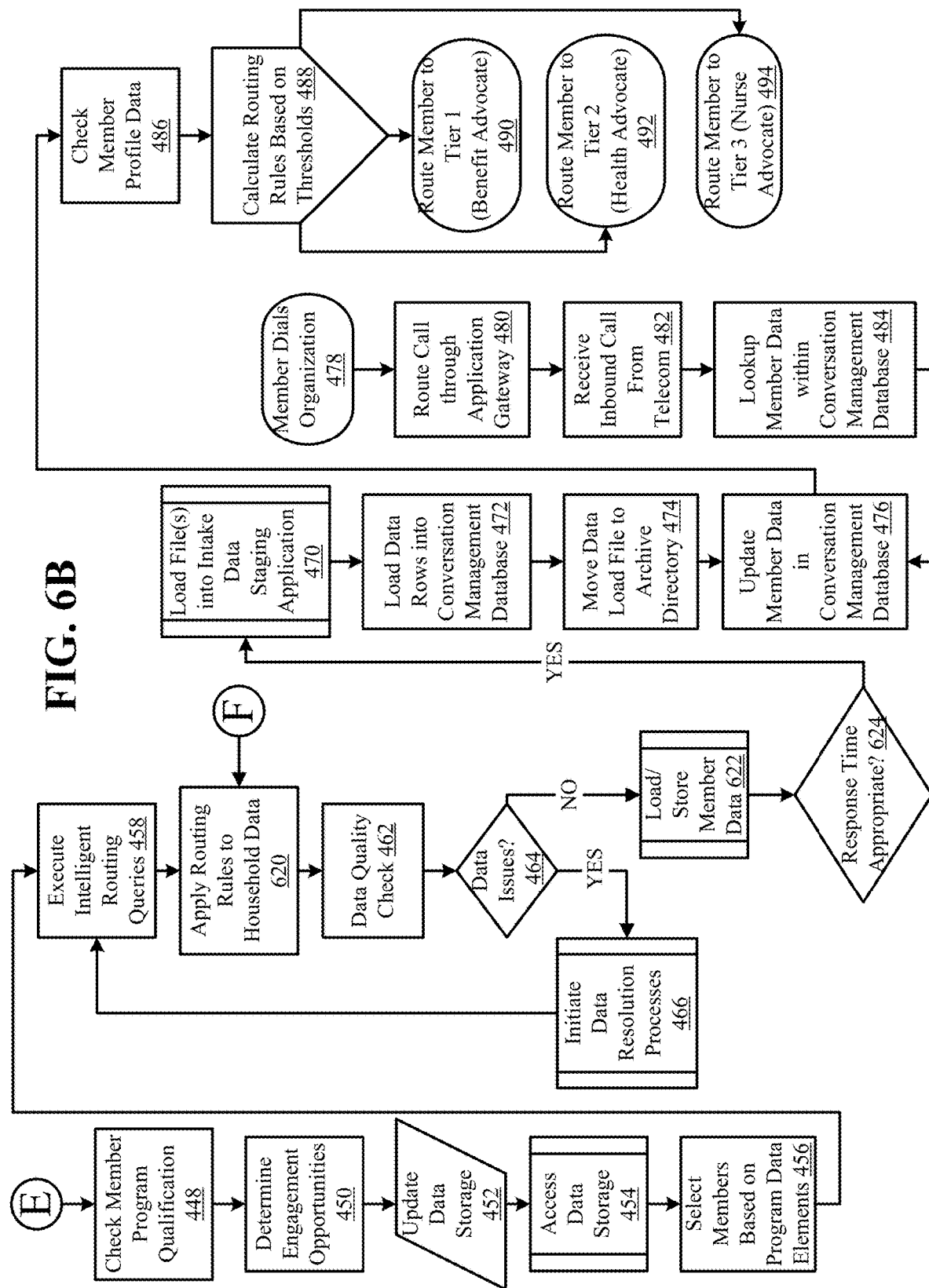
Figure 6C:
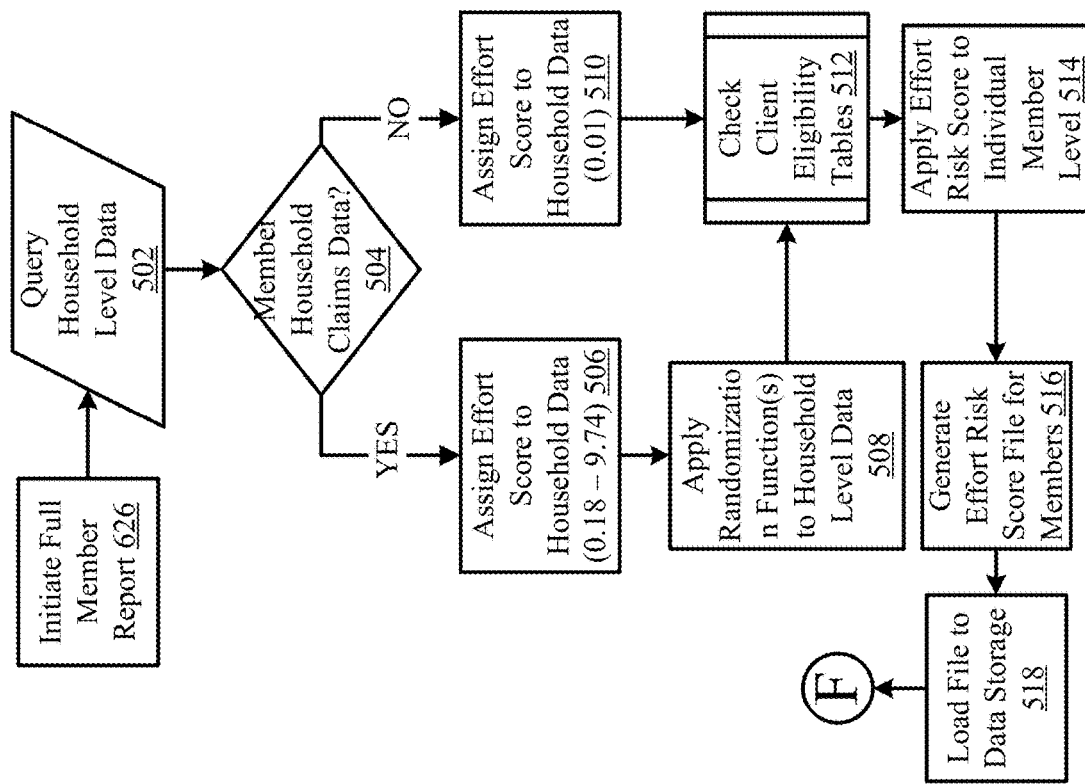

FIGS. 6A through 6C illustrate a further embodiment of the method of FIGS. 4A through 4C for intelligent routing of a member of an organization to an appropriate organization advocate within a network. The reference numbers used in FIGS. 4A through 4C are maintained for identical steps illustrated within FIGS. 6A through 6C. Since the methods of FIGS. 4A through 4C and FIGS. 6A through 6C are substantially identical, only the differences between the figure sets is described in detail below.

As illustrated in FIG. 6B, after step 458, routing rules are applied to member household level data (illustrated as 620). For example, household data may be aggregated to compare Tier 3 routing thresholds that determine Tier 3 routing. If Tier 3 routing thresholds are not surpassed, Tier 2 (effort risk score) is considered for Tier 2 member household routing. If no Tier 2 routing is required, the member household data may be routed to Tier 1 using default routing. The data check (illustrated as 462) may involve the performance of data integrity validations. Examples of integrity validations include, for example, looking for null data elements or duplication of data fields.

Still referring to FIG. 6B, if it is determined that the household data does not have any issues after the quality check is performed (illustrated as 464), the household member data is loaded/stored (illustrated as 622) and it is determined whether the loading response time was appropriate (illustrated as 624). The conversation management processor 110 may query the loaded household member data, and therefore an appropriate time of loading may be real-time or substantially real-time. If the response time is determined appropriate, a routing file is generated for the household member data, and the file is loaded into the intake data staging application (illustrated as 470). For example, it may be possible to utilize files from the source system and calculate the rules in real time. However files are used after the calculations have already been made to define the advocate Tier when the time to do real-time processing back to multiple sources systems takes too long. The amount of time that is too long is based on what the organization has defined as the speed a member call needs to be answered.

As illustrated in FIG. 6C, a full member report is initiated (illustrated as 626) prior to the household level data being queried at step 502. The full report may be a file for employer and individual (E & I) members used to calculate effort risk scores. Furthermore, as illustrated in FIG. 6C, the embodiment of FIGS. 6A through 6C omit steps 520-528 of FIGS. 4A through 4C. This results in step 620 described above following step 518.

According to a further aspect of the disclosure, a system, as previously described herein, specially configured to address technical problems that arise in the context of special needs routing, may include intelligent routing capabilities configured to detect and predict when an individual or group of individuals, such as a family, may be on a diagnostic odyssey or be ambiguously diagnosed. Often times, those who are repeatedly misdiagnosed, or given an unclear diagnosis, require the need of special services or attention from an organization, such as a healthcare provider. Families and individuals with certain special needs have been found to not only utilize healthcare services more than those without special needs, but also see more doctors or other medical professionals and spend significantly more on out-of-pocket expenses.

One technical difficulty associated with the provision and utilization of services for special needs members lies in the identification or diagnosis of the particular condition for which the member may be seeking services or information. For example, some medical conditions may be difficult to diagnose, or are incorrectly diagnosed, particularly those related to developmental or mental disorders. As a result, individuals may require multiple doctor visits which consequently leads to multiple copays, insurance claims and potential phone calls to a healthcare provider.

According to another aspect of the disclosure, a conversation management processor may more accurately identify and direct members to special needs services. When a member places a call to a specially configured system as described herein, the system may authenticate the member to learn the identity of the member or their family for which services may be needed. With this information, a call to back-end systems, such as a secure computer environment as shown in FIG. 2 may be made to identify information known about the caller. Using unique consumer data aligned to the caller, the conversation management processor may service the caller with simplified and personalized scripting, routing, screen pop-ups and other services, based on that member's identification as part of a special needs class. According to a further aspect, the conversation management processor can consistently process and route conversations to a particularly appropriate advocate and/or Tier level. For example, a member may be routed to speak to the same advocate each time the member calls.

Figure 7:
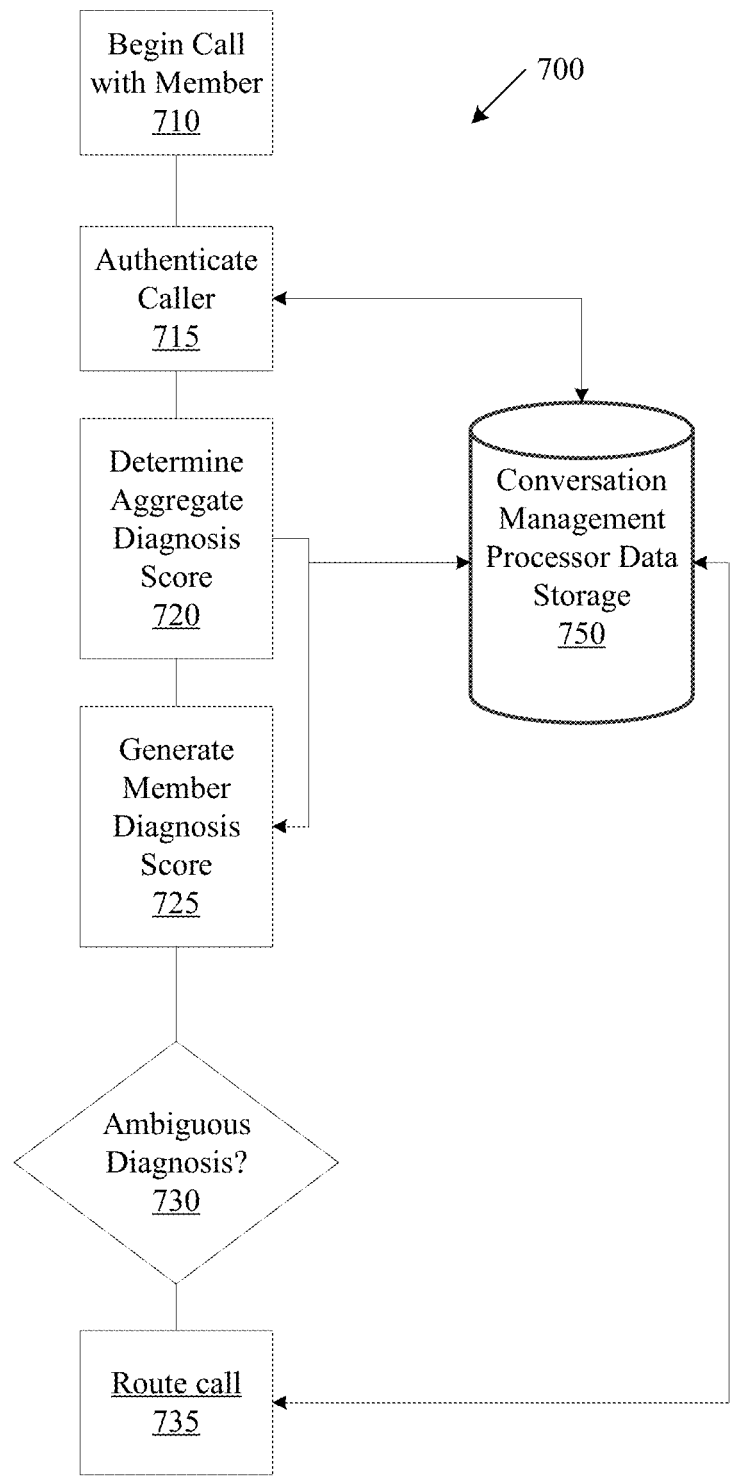
FIG. 7 is a flow diagram depicting a method of using intelligent routing to detect and determine an ambiguous diagnosis, according to one aspect of the present disclosure.

FIG. 7 is a flow diagram depicting a method 700 of using intelligent routing to detect and determine an ambiguous diagnosis, according to one aspect of the present disclosure. One aspect of the present disclosure provides a predictive personalization and intelligent routing system that may allow members to more effectively and efficiently navigate available services offered by an organization, particularly as those services may relate to the organization's members or their families with special needs. As shown in step 710 a secure computing environment may receive or may initiate a call to an organization member. As shown in step 715, a back-end system for conversation management and other services may include a processor to detect and identify a member or class of members to an organization who require services related to certain special needs. The conversation management processor may consult a conversation management processor data storage 750 for information linking the caller to an authorized member of the organization. Identification of a member or members who have been or may be ambiguously diagnosed may lead to several beneficial implementations of the services offered before, during and after a conversation session between a member and an organization. As shown in step 720, the conversation management processor may generate an aggregate diagnosis score. To identify an ambiguously diagnosed member, the system may implement a scoring methodology based on historical data stored in the conversation management processor data storage 750 to generate a score value or other qualifier. A weighted score methodology may be based on an aggregation of hypothesized traits of individuals historically identified to be ambiguously diagnosed. According to one aspect, a quantifiable measurement may be modeled based on a number of criteria.

Exemplary identifiers related to a member's medical data that may be used to model ambiguous diagnoses may include, but are not limited to: members switching between multiple providers, member switching between multiple provider specialties, members having higher non-par provider visits, members with a higher number of denied medical claims, members having claims in multiple geographic regions (states/zip), members having a number of higher physician visits, members with higher randomness in a diagnosis code, members diagnosed with a diagnosis code of low prevalence, members with a high claim count, members with a high-billed and high-allowed amount.

Additional identifiers related to a member's pharmacy data may also be used in conjunction with medical claims data to model and determine an ambiguous diagnosis. Exemplary pharmacy indicators may include, but are not limited to: members with higher count of pharmacy claims requiring prior authorization, members having higher non-par pharmacy claims, members with a higher number of denied pharmacy claims, members using more compound drugs or customized medication, members frequently switching drug brands, members using drugs of low prevalence, members consuming high number of drugs not in formulary list, members with a high ancillary amount compared to typical families.

According to one aspect of the disclosure, the aggregate diagnosis score may be calculated as a portion of the population falling outside of a certain number of standard deviations outside the norm of an aggregated score including factors such as prevalence and randomness of diagnosis codes, variance of provider geography and specialty, number of inpatient stays, and variance of providers seen. Selection based on the diagnostic score may be further subjected to inclusion or exclusion rules such as medical costs within a time period, the percentage of those costs associated with a known condition, and the similarity of that individual to other clusters of individuals.

The historical data when scored according to such a methodology may be used as a baseline to dynamically determine if any given individual is or has been ambiguously diagnosed. As shown in step 725, the conversation management processor may generate a member diagnosis score. The member diagnosis score may be generated similarly to that of the aggregated diagnosis score using the member's data or other data stored in the conversation management processor data storage 750, or provided by the member during the conversation/communication. As shown in step 730, the processor may identify a member who may be ambiguously diagnosed by setting a threshold range around the baseline score and determining a diagnosis classification based on where the member diagnosis score falls in relation to the threshold range. For example, the system may determine that a member diagnosis score outside of three standard deviations of the aggregate diagnosis score is a candidate for special needs services. As shown in step 735, the conversation management processor may route the caller to an appropriate advocate or partner based on the diagnosis classification determination and a rules-based routing structure stored in the conversation management processor data storage 750. The above approach may further include selection based on inclusion or exclusion rules such as medical costs within a time period, the percentage of those costs associated with a known condition, and the similarity of that individual to other clusters of individuals.

Additional aspects of the disclosure allow for the conversation management system to more effectively and proactively establish communication between advocates (those working for and with the organization) and members in need. Aspects of the present system provide for a communications system configured to alert or otherwise establish communication between members requiring special needs. Communication sessions may include, but are not limited to, emails, text messages, chat session, outbound calls to a member, automatically routing a member to an organization partner, display of real-time and pertinent information to an advocate upon an incoming call or a combination of the above. Using aspects of the scoring methodology described above, the system according to the disclosure can determine if and when certain actions should be carried out by advocates as they relate to a member or family member with special needs.

FIG. 8 depicts a scoring table 800a and an action table 800b for an exemplary alert. According to one aspect, scoring factors based on a member's profile and other information may be generated to determine one or more actions to be taken by the predictive personalization and intelligent router system. Scoring factors may be delineated into impact scores or other subsets, such as an Emotional Impact Score 805, a Financial Impact score 810 and a Claim "Fixability" Score 815. Emotional Impact Score 805 factors may include, but are not limited to, a total number of interactions with advocates 820, a total number of freestanding emergency center ("FEC") interactions in the past 90 days 825, the number of previously denied claims 830, the number of denied Prior Authorizations 835, number of gap exceptions 840, and number of family members or children ("SNI Peds") with special needs 845. An exemplary Financial Impact score 810 may be based on, but not limited to, a dollar value of a currently denied claim 850, the dollar value of denied claims in the past 90 days 855, and the current family out-of-pocket spend 860. An exemplary Claim "Fixability Score" 815 may be based on, but not limited to, a percentage of similar claims paid upon further review 865 and the percentage of similar claims paid upon appeal 870. The scoring factor data associated and recorded for the exemplary caller is used, according to one aspect, to classify the Emotional Impact Score 805, Financial Impact Score 810 and Claim "Fixability" Score as either "High," "Medium," or "Low". Alternatively, the Emotional Impact Score 805, a Financial Impact Score 810 and Claim "Fixability" Score 815 may be numerical averages, means or other quantifiable score. The aggregation of those scores may then determine which actions or alerts the predictive personalization and intelligent router system will execute.

Each of the scoring factors may be compared to preset thresholds that, based on historical data, may indicate an ambiguous diagnosis or the need for special services. According to the scoring example, the Emotional Impact Score may be "High" given the scoring factor numbers high numbers (807); the Financial Impact Score may be defined as "High" given the large dollar amounts for each of the scoring factors (813); and the Claim "Fixability" score 815 may be defined as "High" given the high percentages in the scoring factors (817).

An action table 800b lists a number of potential actions to be taken based upon the structured rules to determine High scores of the Emotional Impact Score 805, a Financial Impact score 810 and Claim "Fixability" Score 815. The actions may be in the form of immediate initiations of certain communications or may be stored flags in the system database to initiate actions when a triggering event may occur. According to the scoring example of FIG. 8, the exemplary scores generated may cause an advisor to access a GUI work queue to determine who to call. Alternatively the exemplary scores generated for the member may cause the system to create an immediate informational GUI window or pop-up (875) on an advocates computing device display when an outbound call is initiated, auto route (880) an issue to the appropriate priority team member, which may include an informational pop-up for a team member within the FEC, such as a registered nurse ("RN") or Research advisor, and a delayed informational pop-up (885) displayed upon the next inbound call from the member.

Figure 9A:
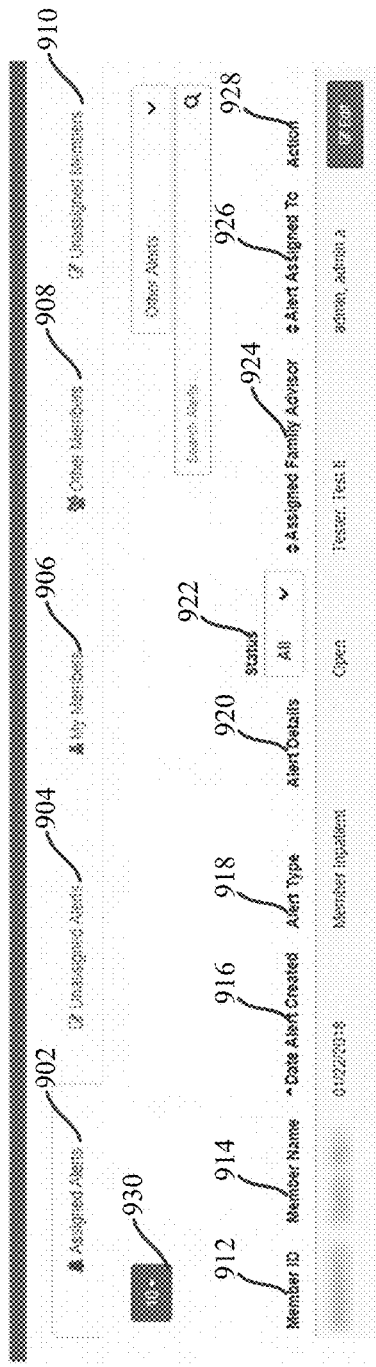
FIGS. 9A-9D depict exemplary diagrams of an alert GUI, according to various embodiments of the present disclosure.

FIGS. 9A-9D depict exemplary diagrams of an alert GUI, according to various embodiments of the present disclosure. FIG. 9A presents a GUI, or portion thereof, listing the current alerts assigned to an organization's advocate or advisor. Multiple tabs presented across the interface include an Assigned Alerts tab 902, an Unassigned Alerts tab 904, a My Members tab 906, an Other Members tab 908, and an Unassigned Members tab 910.

The Assigned Members tab 902 may list the alerts and relevant details of those alerts that have already been assigned to the particular advocate interacting with the interface. The alerts may be characterized and detailed by several columns listing the relevant fields of information for each alert. For example, each alert may include a Member ID 912, a Member Name 914, a Date Alert Created field 918, Alert Details 920, Status 922, Assigned Family Advisor 924, an Alert Assigned To field 926 and an Action option 928. The GUI may also include an alert count drop down 930 which may detail the number of alerts assigned and provide a mechanism for the advocate to navigate to numbered alerts.

Similar listings of alerts that have not been assigned to the advocate may be listed under the Unassigned Alerts tab 904. Members who have been previously assigned to the advocate may be viewed under the My Members tab 906. This tab may provide the advocate with a listing of members and their biographical data as well as any alerts or pending actions associated with those members. The Other Members tab 908 may provide similar information concerning members of the organization that are not assigned to the particular advocate, but are assigned to other advocates. The Unassigned Members tab 910 may provide a listing of members who have yet to be assigned to an advocate.

Figure 9B:
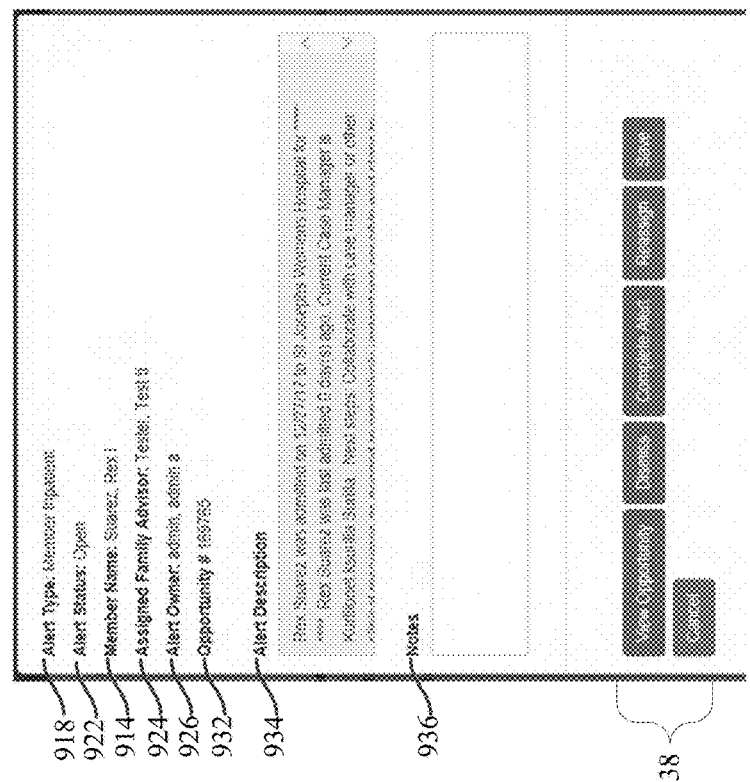

FIG. 9B is a diagram of an exemplary alert pop-up or window for a particular alert. Much like the interface depicted in FIG. 9A, the alert window may list the Alert Type 918, the Alert Status 922, the Member Name 914, the Assigned Family Advisor 924, the Alert Owner (Alert Assigned To) 926 an Opportunity number 932, an Alert Description 934, a Notes field 936 and a number of action 938 to be executed by the advocate.

The Opportunity number 932 may be a reference or index number by with the CM system can record, catalog, retrieve or otherwise track interactions between a member and the system. The Alert Description 934 may include a text window or the like detailing a narrative or text-based description of the member, the members requests, or request history. The Notes field 936 may provide a text-based field allowing the advisor or advocate to record notes about any interactions, recommendations, observations or the like with the member.

Figure 9C:
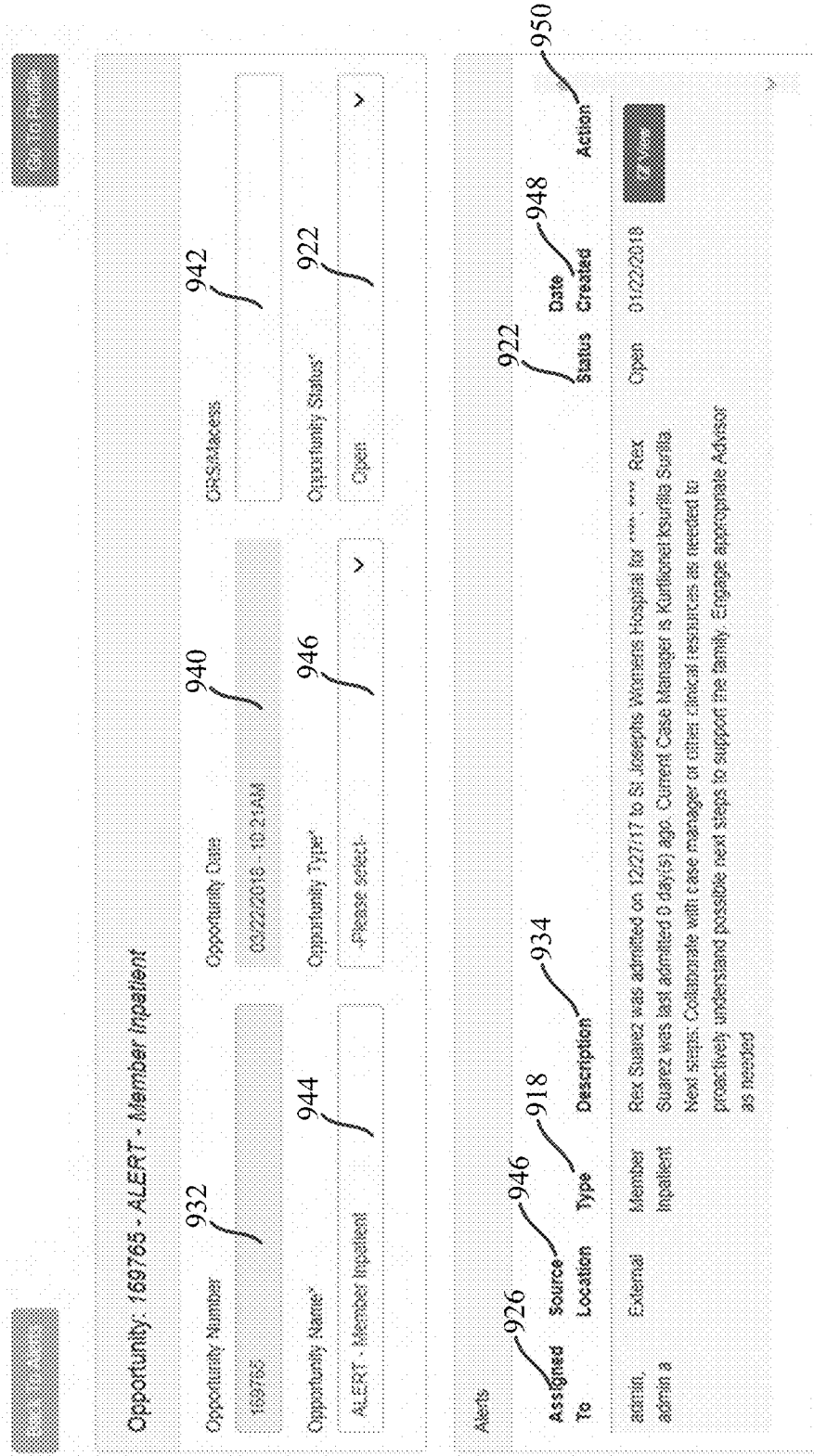

The Action buttons 938 may include links to "View Opportunity" which may display additional details associated with the Opportunity number 932. A "Dismiss" action may close the alert with no further action taken. A Complete Alert action may allow the advisor to indicate that the alert has been satisfied or otherwise handled for the time being. A Reassign action may provide the advisor with the ability to reassign the alert to another advisor. A Save action may save any changes to the alert record made to any of the above-described fields. A Cancel action may simply close the alert window with no further action taken. FIG. 9C is a depiction of an interface displaying the details and other information related to a particular Opportunity. An opportunity is an issue that a family advisor is working on. I.e.—there is an open opportunity that an advisor is working on for the family. An opportunity number is autopopulated with a random number and it allows easy reference a given opportunity without using PHI/PII (e.g.—Hi Sue, I have a question about opportunity 171008 related to family 9647). The Opportunity interface may include the Opportunity number 932, an Opportunity Date 940, ORS/Macess field 942, Opportunity Name 944, Opportunity Type 946 and Opportunity Status 922. "ORS" stands for "Online Routing System" and "MACESS" stands for "Member and Customer Electronic Service and Support." ORS/MACESS indicates if there is an ORS/MACESS number that is associated with this specific opportunity. ORS is the platform that is leveraged for Employer and Individual and MACESS or Community and State. Alert details may be displayed in conjunction with the Opportunity details, which may include, without limitation, an Assigned to Field 926, a Source Location 946, an Alert Type 918, the Description 934, Status 922, Data Created 948, and an Action button 950. The Action button 950 may include an option to view the current alert under the Opportunity, similar to the interface display of FIG. 9B.

Figure 9D:
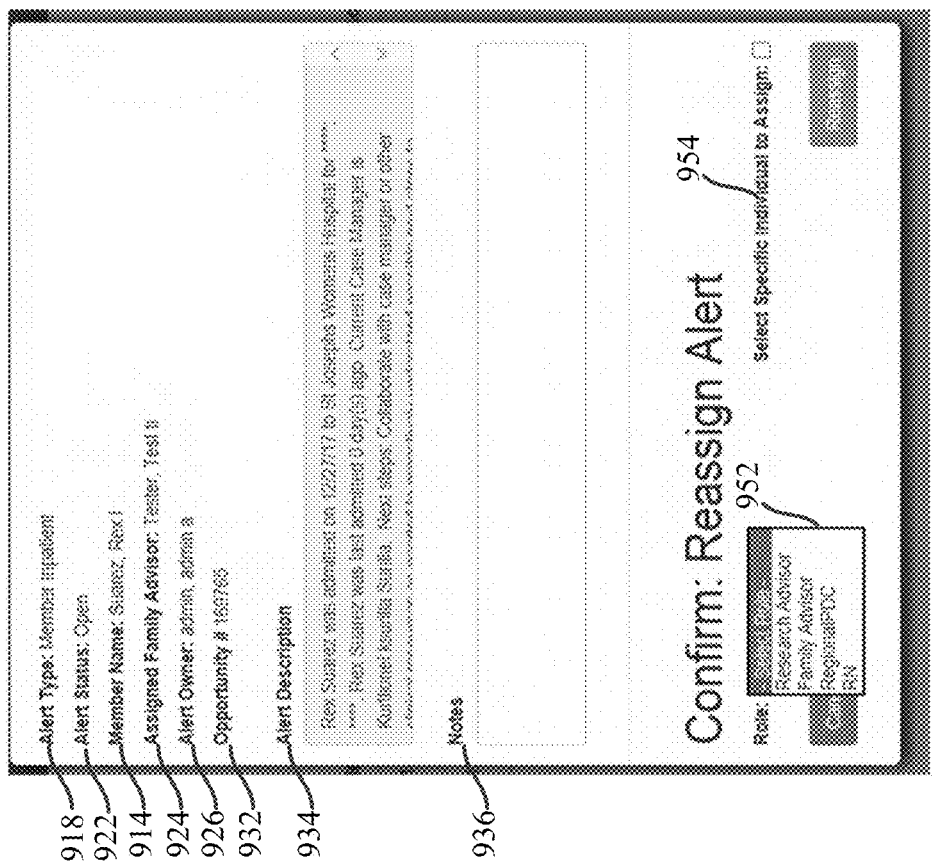

FIG. 9D depicts an interface of an alert through which the advisor may reassign the alert to a different advocate or advisor. The interface may display the same information as the Alert interface depicted in FIG. 9B, and include a drop down window 952 or similar selection window identifying alternatives to whom the alert may be assigned. In the exemplary drop down window 952, alternative to whom the alert may be reassigned may include a research advisor, a family advisor, a Regional PDC or an RN. The reassign interface may further include an reassign option 954 that may allow the advisor to select a specific individual to which the alert may be assigned.

Additional individualized actions that may be triggered based on the alert scoring may include, but are not limited to, an immediate informational pop-up indicating an outbound email to a member, a delayed informational pop-up displayed on the next inbound or outbound call, automatically routing the conversation/communication to an appropriate priority partner, or automatically route the conversation or issue to a research advocate for a resolution. Certain actions may carry with them informational pop-ups that may be generated and displayed on to an advocate through a system user-interface. Additionally, actions may be defined to execute automatically, after a delay, or event triggered.

The proactive alert capability of the specially configured predictive personalization and intelligent routing system may provide organization advocates and partners with real-time critical member data in an actionable format to avoid and prevent issues common to those members with special needs, alert members of upcoming deadlines, and provide efficient issue resolution. The technical advantages may include faster and efficient processing, fewer claims and appeals denials, more accurate and timely information, or the like. The proactive nature of the system may also alert, e.g. using the information pop-ups as described.

Figure 10:
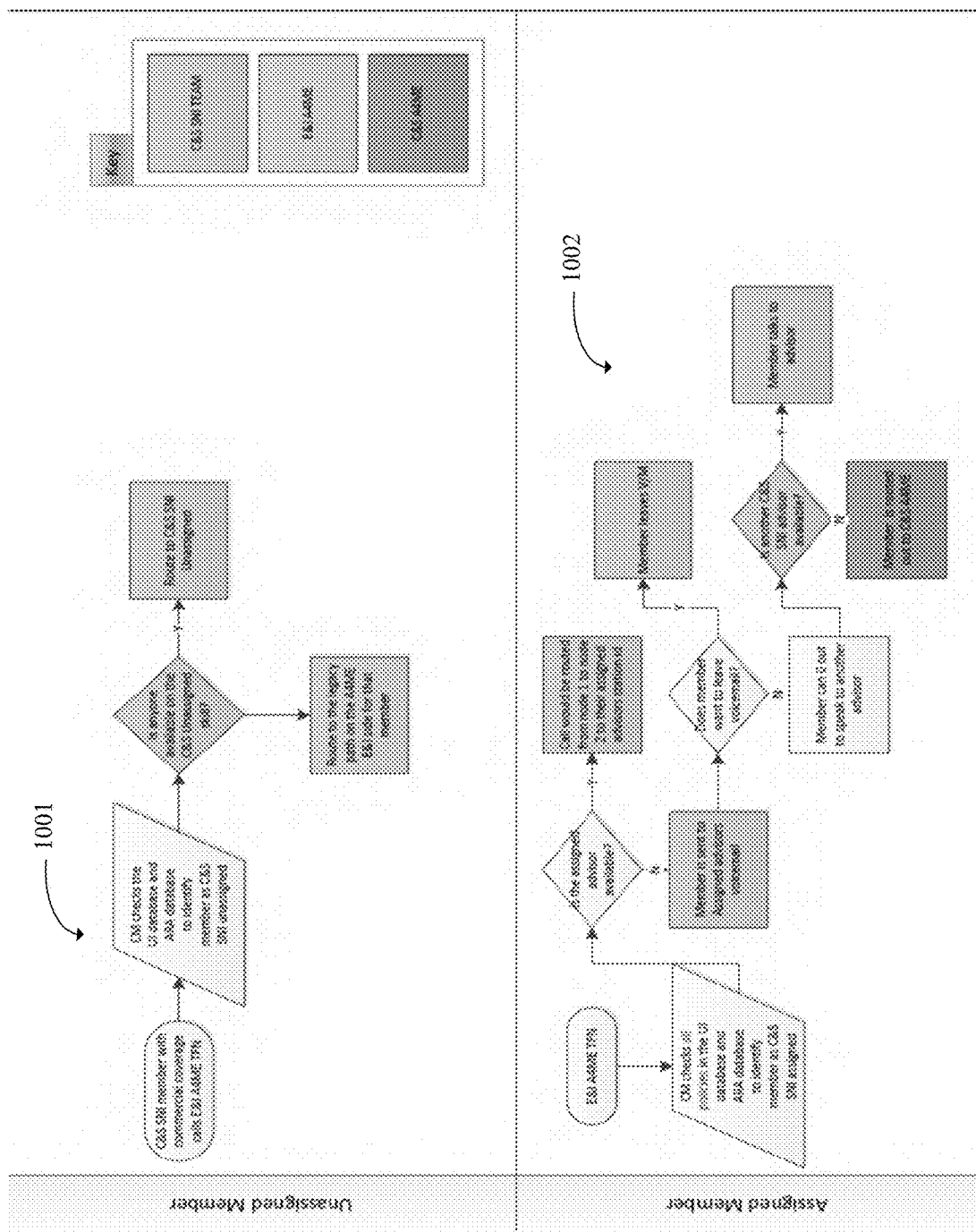
FIG. 10 depicts flow diagrams for handling by the intelligent routing system of an inbound call by a member based on a member's assigned or unassigned status.

According to another aspect of the disclosure the CM system may be configured to appropriately identify and route members requiring special needs who may belong to or subscribe to different levels of service or classes of service to an appropriate advocate. FIG. 10 depicts flow diagrams 1001, 1002 for handling by the CM of an inbound call by a member based on a member's assigned or unassigned status. Routing of an unassigned member (i.e., a member that has not been previously assigned to an advocate) seeking a special need advisor or advocate may be accomplished according to the top flow diagram 1001. An assigned member, on the other hand (i.e., a member who has had an advocate or advisor previously assigned to the member and/or the member's family) may be routed according to the bottom flow diagram 1002 of FIG. 10. Routing by the CM according to the bottom flow diagram, by virtue of having a previously assigned advisor, may present the member with additional technical options through which the member's inbound call may be routed.

Although aspects of the present disclosure are described with respect to embodiments in a healthcare context, it should be understood that various disclosed techniques can be used in numerous other fields of technology in which intelligent routing involves sensitive information. Various applications of the disclosed techniques provide substantial improvements to the functioning of the computer apparatus and the technical environments in which the various applications are implemented.

Moreover, although the present disclosure has been described herein with reference to the accompanying drawings, it is to be understood that the present disclosure is not limited to those precise teachings, and that various other changes and modifications may be made by one skilled in the art without departing from the spirit and scope of the present disclosure.

What is claimed is:

1. A network for intelligently routing an organization's member to an organization representative, comprising:
    an authentication processor configured to authenticate the member using automatic identification;
    a processor configured to analyze spoken content of the member to determine a specialized need of the member; and
    a conversation management processor configured to:
        generate an aggregate diagnosis score, wherein the aggregate diagnosis score is calculated as a portion of a population falling outside of a determined number of standard deviations outside a norm;
        generate a member diagnosis score;
        determine a diagnosis classification of the member, the diagnosis classification of the member being based on a comparison of the member score to the aggregate diagnosis score;
        detect the organization's member or a family member who is a candidate for a special needs service;
        determine a representative to route the member to, based in part on the specialized need of the member; and
        determine actions to be carried out by the representative as they relate to the member or the family member with special needs, based on at least one of the aggregate diagnosis score and the member diagnosis score.

2. The secure network of claim 1 wherein the representative is determined by the member's assigned representative.

3. The secure network of claim 1 wherein the conversation management processor is further configured to generate an opportunity number, the opportunity number being associated with an interaction between the member and the organization representative.

4. The secure network of claim 1 wherein the conversation management processor further determines the representative to route the member to, based in part on an availability of the representative.

5. The secure network of claim 4 wherein the conversation management processor determines if the member is willing to leave a voicemail and generates a prompt for the member to be routed to a different representative.

6. A method for intelligently routing a member of an organization to an organization representative, comprising:
    receiving a communication from a member;
    determining an identity of the member;
    determining an aggregate diagnosis score, wherein the aggregate diagnosis score is calculated as a portion of a population falling outside of a determined number of standard deviations outside a norm;
    determining a member score;
    determining a diagnosis classification of the member using a comparison of the member score to the aggregate diagnosis score;
    detecting the organization's member or a family member who is a candidate for a special needs service;
    determining an organization representative to route the member to, wherein the determination is based in part on the diagnosis classification of the member;
    determining actions to be carried out by the organization representative as they relate to the member or the family member with special needs, based on the member score; and
    providing a user interface to the organization representative to invoke the actions to be carried out in relation to the member or family member with special needs.

7. The method of claim 6, the user interface comprising:
    a Member ID;
    a Member Name;
    a Status;
    an Assigned Family Advisor; and
    an Action list.

8. A system for establishing communication between an organization's member and an organization representative, comprising:
    a conversation management processor configured to:
        generate an aggregate diagnosis score, wherein the aggregate diagnosis score is calculated as a portion of a population falling outside of a determined number of standard deviations outside a norm;
        generate a member diagnosis score;
        determine a diagnosis classification of the member, the diagnosis classification of the member being based on a comparison of the member score to the aggregate diagnosis score;
        generate an alert based in part on the diagnosis classification of the member;
        detect the organization's member or a family member who is a candidate for a special needs service;
        identify a health organization which provides the special needs service;
        provide a description of the alert to the organization representative; and
        define at least one alert action for the organization representative.

9. The system of claim 8 wherein the conversation management processor is further configured to generate an immediate informational pop-up indicating an outbound email to the member.

10. The system of claim 8 wherein the conversation management processor is further configured to generate a delayed information pop-up associated with the member to be displayed on a next call with the member.

11. The system of claim 8 wherein the conversation management processor is configured to route the member to a research advocate.

12. The system of claim 8 wherein the conversation management processor is further configured to determine the organization representative based in part on the alert.

13. The system of claim 8 wherein the conversation management processor is configured to generate a prompt for the organization's member to leave a voicemail for the organization representative.

14. The system of claim 13 wherein the conversation management processor is further configured to generate a prompt for the organization's member to select to speak with a different organization representative.

15. The system of claim 8, the alert comprising an opportunity generated by an interaction between the member and the system.

16. The system of claim 14, the alert further comprising an alert description.

17. The system of claim 8 wherein the conversation management processor is configured to provide an alert interface.

18. The system of claim 17, the alert interface comprising an option to reassign the member to a different organization representative.

\* \* \* \* \*